US008436535B2

(12) United States Patent
Hashimoto et al.

(10) Patent No.: US 8,436,535 B2
(45) Date of Patent: May 7, 2013

(54) INFORMATION ACQUISITION METHOD, INFORMATION ACQUISITION APPARATUS AND DISEASE DIAGNOSIS METHOD

(75) Inventors: Hiroyuki Hashimoto, Yokohama (JP); Katsuaki Kuge, Yokohama (JP); Manabu Komatsu, Kawasaki (JP); Kumi Nakamura, Isehara (JP); Kazuhiro Ban, Ohta-ku (JP); Takeshi Imamura, Chigasaki (JP); Shin Kobayashi, Kawasaki (JP); Tadashi Okamoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 101 days.

(21) Appl. No.: 12/712,131

(22) Filed: Feb. 24, 2010

(65) Prior Publication Data
US 2010/0227308 A1 Sep. 9, 2010

Related U.S. Application Data

(60) Division of application No. 11/319,233, filed on Dec. 28, 2005, now Pat. No. 7,701,138, which is a continuation-in-part of application No. 10/557,402, filed as application No. PCT/JP2004/009788 on Jul. 2, 2004, now abandoned.

(30) Foreign Application Priority Data

| Jul. 2, 2003 | (JP) | ................................ | 2003-270350 |
| Sep. 12, 2003 | (JP) | ................................ | 2003-321418 |
| Sep. 30, 2003 | (JP) | ................................ | 2003-340787 |
| May 25, 2004 | (JP) | ................................ | 2004-154617 |
| Dec. 28, 2004 | (JP) | ................................ | 2004-380052 |

(51) Int. Cl.
*H01J 17/26* (2012.01)

(52) U.S. Cl.
USPC ........................................... 313/564; 435/23

(58) Field of Classification Search .................. 250/288; 313/564; 435/23
See application file for complete search history.

(56) References Cited

U.S. PATENT DOCUMENTS

| 5,372,719 A | 12/1994 | Afeyan et al. |
| 5,453,199 A | 9/1995 | Afeyan et al. |
| 5,641,539 A | 6/1997 | Afeyan et al. |
| 5,808,300 A | 9/1998 | Caprioli |
| 6,603,118 B2 | 8/2003 | Ellson et al. |
| 6,707,038 B2 | 3/2004 | Ellson et al. |
| 6,710,335 B2 | 3/2004 | Ellson et al. |
| 6,809,315 B2 | 10/2004 | Ellson et al. |
| 7,701,138 B2 * | 4/2010 | Hashimoto et al. ........... 313/564 |
| 2005/0282289 A1 | 12/2005 | Ookubo et al. |

FOREIGN PATENT DOCUMENTS
WO 03104794 12/2003

OTHER PUBLICATIONS

Jabs et al. "High performance liquid chromatography and time-of-flight secondary ion mass spectrometry: a new dimension in structural analysis of apolipoproteins", J of Lipid Research, 1986, 27:613-621.*
Caprioli et al. "Molecular imaging of biological samples" localization of peptides and proteins uisng MALDI-TOF MS, Anal. Chem. 1997, 69:4751-4760.*
Kishikawa et al. "Elements and organic substances in epiretinal proliferative tissue excised during vitreous surgery: analysis by time-of-flight secondary-ion mass spectrometry", J of Electron Microscopy, 2003, 52(3):349-354.*
Anna M. Belu, et al., "Enhanced TOF-SIMS Imaging of a Micropatterned Protein by Stable Isotope Protein Labeling", XP-002303726, Analytical Chemistry, vol. 73, No. 2, Jan. 15, 2001, pp. 143-150.
A. Delcorte, et al., "Organic Secondary Ion Mass Spectrometry: Sensitivity Enchancement by Gold Deposition", XP-002303539, Analytical Chemistry, vol. 74, No. 19, Oct. 1, 2002, pp. 4955-4968.
C.M. John, et al., "Static secondary ion mass spectrometry (SSIMS) of biological compounds in tissue and tissue-like matrices", International Journal of Mass Spectrometry and Ion Processes, vol. 161, 1997, pp. 47-67.
Arkady I. Gusev, et al., "Improvement of Signal Intensities in Static Secondary-Ion Mass Spectrometry Using Halide Additives and Substrate Modification", XP008037909, Journal of Mass Spectrometry, vol. 33, 1998, pp. 480-485.
Salehpour, et al., "Laser-Induced Desorption of Proteins", Rapid Communications in Mass Spectrometry, vol. 3, No. 8, 1989, pp. 259-263.
Kachman, et al., "A 2-D Liquid Separations/Mass Mapping Method for Interlysate Comparison of Ovarian Cancers", Analytical Chemistry, vol. 74, No. 8, Apr. 15, 2002, pp. 1779-1791.
Dong, et al., "Characterization of Poly(dimethylsiloxane)s by Time-of-Flight Secondary Ion Mass Spectrometry", Macromolecules, vol. 30, 1997, pp. 63-70.
Belu, et al., "TOF-SIMS Characterization and Imaging of Controlled-Release Drug Delivery Systems", Analytical Chemistry, vol. 72, No. 22, Nov. 15, 2000, pp. 5625-5638.
Roger Michel, et al., "Self-assembled monolayers for polymer and protein cationization with time-of-flight secondary ion mass spectrometry", Journal of Vacuum Science and Technology A. Vacuum, Surfaces, and Films, vol. 18, No. 4, Jul./Aug. 2000, pp. 1114-1118.
Anthony J. Nicola, et al., "Enhancement of Ion Intensity in Time-of-Flight Secondary-Ionization Mass Spectrometry", Journal of the American Society for Mass Spectrometry, vol. 7, 1996, pp. 467-472.
Håkan Nygren, et al., "Bioimaging TOF-SIMS: localization of cholesterol in rat kidney sectons", FEBS Letters, vol. 566, 2004, pp. 291-293.

(Continued)

*Primary Examiner* — Bin Shen
(74) *Attorney, Agent, or Firm* — Fitzpatrick, Cella, Harper & Scinto

(57) ABSTRACT

An information acquisition method for acquiring information on a target object, that includes a step of promoting ionization of the target object using a substance for promoting ionization of the target object to cause the target object to emit, and a step of acquiring information on the mass of the flew target object using time-of-flight secondary ion mass spectrometry.

4 Claims, 10 Drawing Sheets

OTHER PUBLICATIONS

Thomas P. Roddy, et al., "Identification of Cellular Sections with Imaging Mass Spectrometry Following Freeze Fracture", XP-002303725, Analytical Chemistry, vol. 74, No. 16, Aug. 15, 2002, pp. 4020-4026.

Peter Sjövall, et al., "Imaging of Membrane Lipids in Single Cells by Imprint-Imaging Time-of-Flight Secondary Ion Mass Spectrometry", XP-001176022, Analytical Chemistry, vol. 75, No. 14, Jul. 15, 2003, pp. 3429-3434.

Peter J. Todd, et al, "Organic ion imaging of biological tissue with secondary ion mass spectrometry and matrix-assisted laser desorption/ionization", XP008037954, Journal of Mass Spectrometry, vol. 36, 2001, pp. 355-369.

Kuang Jen Wu, et al., "Matrix-Enhanced Secondary Ion Mass Spectrometry: A Method for Molecular Analysis of Solid Surfaces", XP-002303540, Analytical Chemistry, vol. 68, No. 5, Mar. 1, 1996, pp. 873-882.

Lenaerts, et al., "Imaging TOF-SIMS for the surface analysis of sliver halide microcrystals", Applied Surface Science, vol. 203-204, 2003, pp. 614-619.

Winkelmann, et al., "Chemically patterned, metal oxide based surfaces produced by photolithographic techniques for studying protein- and cell-surface interactions I: Microfabrication and surface characterization", Biomaterials, vol. 24, 2003, pp. 1133-1145.

Chevolot, et al., "Synthesis and Characterization of a Photoactivatable Glycoaryldiazirine for Surface Glycoengineering", Bioconjugate Chem., vol. 10, 1999, pp. 169-175.

Hensel, et al., "Electrospray Sample Preparation for Improved Quantitation in Matrix-assisted Laser Desorption/Ionization Time-of-flight Mass Spectrometry", Rapid Communications in Mass Spectrometry, vol. 11, 1997, pp. 1785-1793.

Nicola et al., "Enhancement of Ion Intensity in Time-of-Flight Secondary-Ionization Mass Spectrometry", American Society for Mass Spectrometry, 1996; vol. 7, No. 5, pp. 467-472.

Chinese Office Action dated Apr. 27, 2012 from Chinese Patent Appln. No. 2010-10275246.1, with English Translation.

* cited by examiner

Field of view: 199.0×199.0 µm²  Mor AgNO3 on Si C0710-

Morphiceptin+Ag    total ion
mc:2 tc:2897       mc:3664 tc:4.41e+7

INFORMATION ACQUISITION METHOD, INFORMATION ACQUISITION APPARATUS AND DISEASE DIAGNOSIS METHOD

This application is a divisional of U.S. patent application Ser. No. 11/319,233, filed Dec. 28, 2005, now U.S. Pat. No. 7,701,138, issued Apr. 20, 2010, which is a continuation-in-part application of U.S. patent application Ser. No. 10/557,402, filed on Nov. 18, 2005 (abandoned), which is the National Stage of International Application No. PCT/JP2004/009788, filed on Jul. 2, 2004, the contents of each of which are incorporated by reference herein.

BACKGROUND OF THE INVENTION

1. Field of the Invention

The present invention relates to a method for acquiring information, an apparatus for acquiring information and a method for diagnosing disease, and more particularly to a method or apparatus that uses Time of Flight Secondary Ion Mass Spectrometry (TOF-SIMS).

2. Related Background Art

The progress in genomics in recent years has led to a rapid focus on the importance of analysis of proteins that are gene products present in vivo, and on an analysis of a metabolite existing as an end product in vivo, too.

The importance of analyzing the expression and functions of proteins has been indicated before now and analysis methods have developed. A field of study in metabolite is called "metabonomics" or "metabolomics". Specifically, these methods have been practiced using a combination of:

(1) separation and purification through two-dimensional electrophoresis or high-performance liquid chromatography (HPLC), and (2) a detection system such as radiometry, optical analysis or mass spectrometry.

Developments in the technology for analyzing proteins include the construction of databases through proteome analysis (exhaustive analysis of protain in a cell), which may be considered the foundation of protein analysis. Devices that are based on databases obtained thereby can be roughly classified into diagnostic devices and devices for development of innovative drugs (screening of drug candidates). However, with respect to each form of application, the conventional methods involve problems with respect to analysis time, throughput, sensitivity, analyzing ability, flexibility and the like. Thus there has been a need for a device that differs to the conventional methods in these respects and which enables miniaturization, enhanced speed and automation. Accordingly, the development of the so-called "protein chip" in which protein is accumulated at a high density is attracting attention as a method that will meet these needs.

A target molecule captured on a protein chip can be detected by the various detection means described below.

In methods involving mass spectrometry (MS) of protein, in recent years Time of Flight Secondary Ion Mass Spectrometry (hereinafter, abbreviated to "TOF-SIMS") has been used as a high sensitivity mass spectrometry means or surface analysis means. The term "TOF-SIMS" refers to an analysis method for investigating what type of atoms or molecules are present on the outermost surface of a solid sample. TOF-SIMS has the following characteristics. That is, it can detect a trace constituent of $10^9$ atoms/cm$^2$ (amount corresponding to $1/10^5$ of 1 atomic layer of the outermost surface), it can be applied to both organic matter and inorganic matter, it can measure all chemical elements or compounds present on a surface, and it is capable of imaging secondary ions from substances present on a sample surface.

The principles of this method are briefly described below.

In a high vacuum, a high speed pulsed ion beam (primary ion) is applied to the surface of a solid sample, whereby the constituents of the surface are released into the vacuum by a sputtering phenomenon. Ions (secondary ions) having a positive or negative charge that are generated at this time are converged in one direction by an electric field and detected at a position separate from the sample by a fixed distance. When a pulsed primary ion is applied to the solid surface, secondary ions having various masses are generated in accordance with the composition of the sample surface. Since the lighter an ion is the faster it will emit, and conversely, the heavier the ion is the slower it will emit, it is possible to analyze the mass of the generated secondary ions by measuring the time from the generation of secondary ions until the detection (time of flight). Because only secondary ions generated on the outermost surface of a solid sample are released into the vacuum when a primary ion is irradiated on the sample, information on the outermost surface (depth of approximately several nm) can be obtained. Since a primary ion fluence in TOF-SIMS is remarkably small, an organic compound is ionized in a state where it retains its chemical structure, and the structure of the organic compound can be known from the mass spectrum. However, when analyzing artificial high polymers such as polyethylene or polyester, biopolymers such as protein, and the like using TOF-SIMS under normal conditions, small decomposed fragment ionic species are formed and it is thus generally difficult to know the original structure of the sample. When a solid sample is an insulator, the insulator can be analyzed by using an additional pulsed electron beam during gaps in the pulses of irradiation of a primary ion, to thereby neutralize positive charges accumulating on the solid surface. In addition, in TOF-SIMS, it is also possible to generate an ion image (mapping) of the sample surface by scanning a primary ion beam across the sample surface.

Examples of protein analysis using TOF-SIMS include an analysis in which one part of a specific protein is labeled with an isotope such as $^{15}$N and imaging of the protein is detected using a secondary ion such as $C^{15}N^-$ (A. M. Belu et al., Anal. Chem., 73, 143 (2001)). Further, a study has been reported which estimates the kinds of proteins based on the kinds of fragment ionic species (secondary ions) corresponding to amino acid residues and the relative intensities thereof (D. S. Mantus et al., Anal. Chem., 65, 1431 (1993)). In addition, a study that investigated the limits of detection for TOF-SIMS for protein adsorbed on substrates of various kinds is known (M. S. Wagner et al., J. Biomater. Sci. Polymer Edn., 13, 40 7 (2002)).

Another method of mass spectrometry that employs a protein as a target is a method utilizing field emission (U.S. Pat. No. 5,952,654). In this method, the protein is subjected to covalent bonding or coordinate bonding on a metal electrode through a fissionable open group in accordance with an applied energy, and the protein is introduced into a mass spectrometer by applying a high electric field.

However, since conventional mass spectrometry does not analyze the target substance (e.g. content in cell) itself, but rather takes an eluted protein or the like as its object, there are limitations to the information obtained.

The MALDI method and the SELDI method, an improved version of the MALDI method, are the softest ionization methods of those currently known. They possess excellent characteristics that enable ionization of a protein with a high molecular weight that is susceptible to breakage as it is, and then detection of the parent ion or an ion conforming thereto.

This is currently one of the standard ionization methods when analyzing the mass of a protein. However, when applying these methods to mass spectrometry of a protein chip it is difficult to obtain a two-dimensional distribution image (imaging using mass information) of a protein that has a high spatial resolution due to the presence of a matrix substance. More specifically, although the laser beam itself that is the excitation source can be readily condensed to a diameter of about 1 to 2 μm, a matrix substance present in the vicinity of the protein that is the analysis target is vaporized by the laser beam and ionizes, and therefore the spatial resolution obtained when generating a two-dimensional distribution image of the protein by above method is generally only at a level of about 100 μm. Also, in order to scan the condensed laser beam it is necessary to operate a lens and mirror in an intricate manner. In short, when generating a two-dimensional distribution image of a protein by the above method it is difficult to scan the laser beam, and the technique is confined to a method that moves a sample stage on which the sample to be analyzed is placed. When attempting to obtain a two-dimensional distribution image of a protein at a high spatial resolution, a method that moves a sample stage is generally not preferable.

In comparison with the above methods, because the TOF-SIMS method uses a primary ion, convergence and scanning thereof can be easily performed. Thus, a secondary ion image (two-dimensional distribution image) of a high spatial resolution can be obtained, and it is possible to obtain a spatial resolution of a level of about 1 μm. However, with respect to a target substance (e.g. content in cell) on a substrate, when TOF-SIMS measurement is performed under normal conditions, as described above it is generally difficult to know the original structure of the target substance because almost all of the generated secondary ions are small decomposed fragment ionic species. Therefore, for a sample such as a protein chip in which a plurality of proteins are disposed on a substrate, to obtain a secondary ion image (two-dimensional distribution image) of a high spatial resolution with which the kinds of the proteins can be distinguished, it is necessary to employ some kind of contrivance. It is also necessary to employ some kind of contrivance to distinguish metabolic substances in cell by kind. The above method of A. M. Belu et al. is a method in which one part of a specific protein is labeled with an isotope to allow the high spatial resolution of TOF-SIMS to be adequately exploited. However, providing a specific protein with an isotope label for each measurement is not a common technique. In the method of D. S. Mantus et al. that estimates the kinds of proteins from the kinds of fragment ionic species (secondary ions) corresponding to amino acid residues and the relative intensities thereof, difficulties arise when there is a mixture of proteins having similar amino acid structures.

When applying the TOF-SIMS method to tissue from a living organism, for example, a protein molecule, when peptide chains comprising the protein molecule are in a "held state", the ionization efficiency of secondary ions declines to a large degree. Also, in measurement using TOF-SIMS, since irradiation of a primary ion is conducted in a high vacuum, drying treatment is conducted for the measurement target sample beforehand. If interaction is generated between protein molecules and other biological materials present in the tissue from a living organism at the time of drying treatment and causes aggregation through intermolecular bonding, the ionization efficiency of secondary ions declines still further.

Accordingly, it is preferable to analyze an amount of specific protein molecules present in tissue from a living organism at a high detection sensitivity and with high quantitativeness, and to release the state of peptide chains comprising a protein molecule that are in a "held state" within the tissue to conduct two-dimensional imaging with respect to the distribution state of the abundance of specific protein molecules on a section of the tissue. Further, it is preferable to inhibit interaction between protein molecules and other biological materials, and retain a state whereby secondary ions are generated at a high efficiency from the peptide chains that have been released from the "holding" state. Alternatively, it is preferable to promote and augment generation of secondary ions from a protein molecule present on a section of tissue from a living organism.

Meanwhile, in the TOF-SIMS method, although ion sputtering is performed by irradiating with primary ions the molecule that is the target of analysis, differences in sputtering efficiency arise in accordance with the form of a surface on which primary ion irradiation is conducted. As a result, a difference also arises in the efficiency of generation of secondary ions deriving from the molecule that is the target of analysis. This is a factor that causes variations in the accuracy of analysis. Therefore, it is preferable to also inhibit fluctuations in the efficiency of generation of secondary ions that stem from variations in the forms of surfaces on which primary ion irradiation is conducted. However, the methods disclosed heretofore have not necessarily been adequate in overcoming these points.

SUMMARY OF THE INVENTION

According to an aspect of the present invention, there is provided an information acquisition method for acquiring information on a target object, characterized in that it comprises the steps of:

promoting ionization of the target object using a substance for promoting ionization of the target object to cause the target object to emit; and acquiring information on the mass of the flew target object using a time-of-flight secondary ion mass spectrometry.

The target object is preferably a protein.

The flew target object is preferably any of:

(1) an ion corresponding to a parent molecule of the target object;

(2) an ion corresponding to a mass obtained by addition to a parent molecule of the target object of an atom or a cluster of a specific metal element;

(3) an ion corresponding to a mass obtained by addition to a parent molecule of the target object of an atom or a cluster of a specific metal element and further addition thereto of any number of from 1 to 10 atoms of at least one selected from the group consisting of hydrogen, carbon, nitrogen and oxygen;

(4) an ion corresponding to a mass obtained by addition to a parent molecule of the target object of an atom or a cluster of a specific metal element, and further addition thereto of any number of from 1 to 10 atoms of at least one selected from the group consisting of hydrogen, carbon, nitrogen and oxygen, and elimination therefrom of any number of from 1 to 10 atoms of at least one selected from the group consisting of hydrogen, carbon, nitrogen and oxygen;

(5) an ion corresponding to a mass obtained by addition to a partial structure of the target object of an atom or a cluster of a specific metal element;

(6) an ion corresponding to a mass obtained by addition to a partial structure of the target object of an atom or a cluster of a specific metal element, and further addition thereto of any number of from 1 to 10 atoms of at least one selected from the group consisting of hydrogen, carbon, nitrogen and oxygen; and (7) an ion corresponding to a mass obtained by addition to a partial structure of the target object of an atom or an cluster of a specific metal element, and further addition thereto of any number of from 1 to 10 atoms of at least one selected from the group consisting of hydrogen, carbon, nitrogen and oxygen, and elimination therefrom of any number of from 1 to 10 atoms of at least one selected from the group consisting of hydrogen, carbon, nitrogen and oxygen.

The information on a state of two-dimensional distribution of the target object obtained by scanning of a primary ion is preferably acquired based on a result of detection of the flew target object.

The step of promoting ionization of the target object is preferably comprised of the steps of: contacting the target object and the substance for promoting ionization, and then irradiating a primary ion on the contacted part. The contacting step is preferably performed utilizing a silver mirror reaction.

The target object in the information acquisition method is preferably a content of cell. The content of cell is preferably a metabolite. The metabolite is preferably a drug metabolite. A mass of the content of cell preferably falls within the range of 50 to 2000.

The present invention further provides a chemical composition analysis method for analyzing the chemical composition of a target object using mass spectrometry, that is characterized in that it comprises a step of promoting ionization of the target object using a substance for promoting ionization of the target object to cause the target object to emit, and a step of analyzing the chemical composition of the target object based on information regarding the target object that flew.

The present invention further provides an information acquisition apparatus for acquiring information from a target object using mass spectrometry, characterized in that it comprises means for performing chemical modification of the target object, means for generating from the target object secondary ions that can be distinguished by the chemical modification, and means for detecting the secondary ions.

According to another aspect of the present invention, there is provided an information acquisition method for acquiring information on the mass of a target object using a time-of-flight mass spectrometer, characterized in that it comprises the steps of:

applying a substance for promoting ionization of the target object;

ionizing the target object using a focused, pulsed and scannable primary beam to cause the target object to emit; and acquiring information on the mass of the flew target object using a time-of-flight mass spectrometer.

The primary beam is preferably an ion beam.

The step of applying a substance for promoting ionization of the target object is preferably a step using an aqueous solution comprising an ionization-promoting substance, and is conducted in a one-step process. The substance for promoting ionization of the target object is preferably a water-soluble substance. Alternatively, the substance for promoting ionization of the target object is preferably comprised of an atom of at least one selected from the group consisting of noble metals and alkali metals. The substance for promoting ionization of the target object is preferably comprised of an atom of either Ag or Na.

The information on the mass of a target object is preferably information on a mass of any of:

(1) an ion corresponding to a mass obtained by addition to the mass of a parent molecule of the target object of the mass of an atom of at least one selected from the group consisting of noble metals and alkali metals;

(2) an ion corresponding to a mass obtained by addition to the mass of a parent molecule of the target object of the mass of an atom of at least one selected from the group consisting of noble metals and alkali metals and further addition thereto of the mass of any number of from 1 to 10 atoms of at least one selected from the group consisting of hydrogen, carbon, nitrogen and oxygen;

(3) an ion corresponding to a mass obtained by addition to the mass of a parent molecule of the target object of the mass of an atom of at least one selected from the group consisting of noble metals and alkali metals and further addition thereto of the mass of any number of from 1 to 10 atoms of at least one selected from the group consisting of hydrogen, carbon, nitrogen and oxygen, and elimination therefrom of the mass of any number of from 1 to 10 atoms of at least one selected from the group consisting of hydrogen, carbon, nitrogen and oxygen.

At least one step of a step of preparing the target object and the step of applying a substance for promoting ionization of the target object is preferably conducted by applying droplets. The droplet is preferably comprised of water and a surfactant.

The above focused, pulsed and scannable primary beam is selected from the group consisting of an ion, a neutral particle, an electron, and a focused, pulsed and scannable laser beam, and an ion is preferable. In this case, the information acquisition method is a method using time of flight secondary ion mass spectrometry.

The present invention also provides the above method characterized in that the target object is a protein.

The present invention further provides the above method characterized in that a step for applying either the target object or a substance for promoting ionization, or both thereof, is a step using an ink-jet method.

The present invention still further provides the above information acquisition method, characterized in that the step for applying a substance for promoting ionization of a target object is a step using an aqueous solution containing an ionization-promoting substance. The above information acquisition method is also characterized in that the substance for promoting ionization of a target object is an aqueous substance, and the substance contains at least one member of the group consisting of metallic elements and alkali metals.

The present invention further provides an information acquisition apparatus that is an apparatus for obtaining information on a target object for measurement using time of flight secondary ion mass spectrometry that has an ion beam irradiation means, an ion beam polarization means, and a detection means for detecting secondary ions from the target object for measurement, that is characterized in that it comprises means for applying droplets.

The present invention further provides the above information acquisition apparatus, characterized in that the means for applying droplets is means using an ink-jet method.

According to a further aspect of the present invention, there is provided an information acquisition method for acquiring information on the mass of a constituent of a target object using a time-of-flight mass spectrometer to obtain information on a distribution of the constituent based on the acquired information, characterized in that the method comprises the steps of:

preparing a sample comprising a constituent of tissue from a living organism as the target object;

conducting a treatment for promoting ionization of an ionic species deriving from the constituent;

irradiating the target object with a focused ion beam to cause the ionic species deriving from the constituent to emit; and measuring an intensity of the flew ionic species using a time-of-flight mass spectrometer to obtain information on a distribution of the constituent based on the measured value.

The treatment for promoting ionization is preferably the application of a substance for promoting ionization of the ionic species deriving from the constituents to the constituent.

The treatment for promoting ionization is preferably the decomposition of the constituent by a digestive enzyme.

The treatment for promoting ionization preferably consists of both the decomposition of the constituent by a digestive enzyme and the application of a substance for promoting ionization of the ionic species deriving from the constituents to the constituent. Both the decomposition and the application are preferably carried out by an ink-jet method.

According to a still further aspect of the present invention, there is provided an information acquisition method for acquiring information on the mass of a constituent of a target object using a time-of-flight mass spectrometer to obtain information on a distribution of the constituent based on. the acquired mass information, characterized in that the method comprises the steps of:

preparing a sample comprising a constituent of tissue from a living organism;

contacting the sample with the surface of a substrate to transfer at least one part of the constituent to the substrate;

irradiating a focused ion beam onto the substrate to which at least one part of the constituent was transferred as the target object to cause an ionic species deriving from the constituent to emit; and measuring an intensity of the flew ionic species using a time-of-flight mass spectrometer to obtain information on a distribution of the constituent based on the measured value.

The surface of the substrate with which the sample is preferably contacted comprises a substance for promoting ionization of the ionic species deriving from the constituents. Alternatively, the surface of the substrate with which the sample is preferably contacted has chemically treated for promoting transfer of the constituent to the substrate. The chemical treatment is preferably the introducing of a maleimide group onto the substrate surface.

The constituent of tissue from a living organism in the information acquisition method is preferably a cell.

According to a further aspect of the present invention, there is provided a method for detecting whether a substance particular to a disease exists in a specimen or not which utilizes the above information acquisition method.

According to a still further aspect of the present invention, there is provided an information acquisition apparatus for acquiring information on a target object using time-of-flight secondary ion mass spectrometry, characterized in that the apparatus comprises a means for contacting the target object with a substance for promoting ionization of the target object and a means for irradiating with an ion beam an area of contact between the target object and the substance for promoting ionization of the target object, wherein information on the mass of the target object at least one part of which object was ionized is acquired by the irradiation from the irradiating means.

According to a still further aspect of the present invention, there is provided a disease diagnosis method, characterized in that diagnosis of a disease is conducted by utilizing the information acquisition method of the present invention. A protein is preferably comprised in the constituent of tissue from a living organism, and the diagnosis is conducted by utilizing a state of distribution of a flew ionic species that derive from a peptide of a mass in a range of 500 to 5000 comprised in the protein.

The present invention further provides a disease diagnosis method, characterized in that diagnosis of a disease is conducted by utilizing the information acquisition method of the present invention.

An information acquisition apparatus that acquires information on the mass of a constituent comprised of a target object using a time-of-flight mass spectrometer to obtain information on a distribution of the constituents based on the acquired mass information, characterized in that it comprises:

a means for contacting the constituents with a substrate surface to transfer at least one part of the constituents to the substrate side;

a time-of-flight mass spectrometer that employs the substrate to which at least one part of the constituent was transferred as the target object, and irradiates the target object with a focused ion beam to cause ionic species deriving from the constituents to emit, to measure intensities of the flew ionic species; and a means for analyzing a measurement result for obtaining information on a distribution state of the constituents based on the measured value.

Where necessary herein, a substance for promoting ionization of ionic species may be referred to as a "sensitizer". Also, where necessary herein, the act of contacting a sample containing constituents of tissue from a living organism with the surface of a substrate to transfer at least one part of the constituents to the substrate surface may be referred to as "transfer". Further, the term "analysis" may be used herein in place of the term "information acquisition".

According to the present invention, there can be provided a method for obtaining a two-dimensional distribution image of high spatial resolution for each kind of target object, as well as an information acquisition apparatus that can be favorably applied thereto. According to the information acquisition method of the present invention, generation of secondary ions deriving from constituents of tissue from a living organism can be efficiently conducted, and the distribution state of constituents of tissue from a living organism can be easily determined at a high sensitivity. In addition, the distribution state of constituents of tissue from a living organism can be determined with excellent quantitative properties.

BRIEF DESCRIPTION OF THE DRAWINGS

FIGS. 1A and 1B show enlarged views of sections of positive secondary ion mass spectra according to Example 4, in which FIG. 1A shows a measured spectrum, and FIG. 1B shows a theoretical spectrum calculated on the basis of the isotope ratio;

FIGS. 2A, 2B and 2C show enlarged views of sections of positive secondary ion mass spectra according to Example 9, in which FIG. 2A shows a measured spectrum, FIG. 2B shows a theoretical spectrum calculated on the basis of the isotope ratio, and FIG. 2C is an image generated by imaging using corresponding secondary ion peak in an obtained secondary ion mass spectrum;

FIGS. 4A, 4B and 4C show enlarged views of sections of positive secondary ion mass spectra according to Example 13, in which FIG. 4A shows a measured spectrum, FIG. 4B shows a theoretical spectrum calculated on the basis of the isotope ratio, and FIG. 4C is an image generated by imaging using corresponding secondary ion peak in an obtained secondary ion mass spectrum;

FIGS. 7A, 7B and 7C show enlarged views of sections of positive secondary ion mass spectra according to Example 14, in which FIG. 7A shows the spectrum of peptide 1), FIG. 7B shows the spectrum of peptide 2), and FIG. 7C shows the spectrum of peptide 3);

FIGS. 11B, 11C and 11D conceptually show, as examples, with respect to a cleaved slice of a sample of tissue from a living organism (FIG. 11A), action and binding of a sensitizer to protein components present on the slice surface generated by applying of a solution containing the sensitizer onto the slice surface, as well as images generated by TOF-SIMS imaging of protein components present on the slice surface that were subjected to action and binding treatment of the sensitizer; FIGS. 12B, 12C and 12D conceptually show, as examples, transference to a transfer plate of protein components present on the surface of a slice of a sample of tissue from a living organism (FIG. 12A), and images generated by TOF-SIMS imaging of protein components transferred to a transfer plate.

DETAILED DESCRIPTION OF THE PREFERRED EMBODIMENTS

Figure 1A:
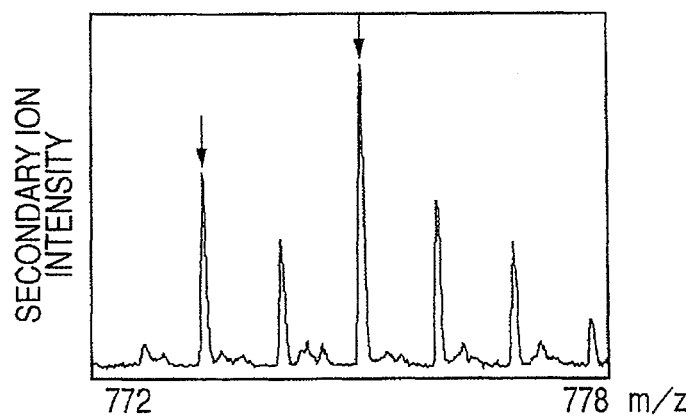

Where necessary herein, a substance for promoting ionization of ionic species may be referred to as a "sensitizer". Also, where necessary herein, the act of contacting a sample containing constituents of tissue from a living organism with the surface of a substrate to transfer at least one part of the constituents to the substrate surface may be referred to as "transfer". Further, the term "analysis" may be used herein in place of the term "information acquisition".

I. Description of the Invention Relating to the First Aspect of the Present Invention The first aspect of the present invention is characterized in that the target object is caused to emit using a substance for promoting ionization of a target object, to obtain information on the mass of secondary ions that can distinguish the target object that flew. The first aspect herein is also characterized in that (performing imaging of) the state of two-dimensional distribution of the target object is detected that can be obtained by scanning of a primary ion.

A substance for promoting ionization of a target object according to the present invention may be applied thereto by any of:

(1) applying the substance after disposing a target object on a substrate, (2) previously applying the substance with respect to a specified one kind or plurality of kinds of target object disposed on a substrate, and (3) applying the substance to a substrate surface prior to disposing a target object on the substrate.

As an example of a method of applying the substance, chemical modification may be mentioned.

Of the techniques listed in the above (1) to (3), the technique of the above (1) can be applied to analysis of every form of target object, and is thus a highly flexible general-purpose technique. When applying a substance promoting ionization with respect to a target object distributed two dimensionally on a substrate, care is required to ensure the process involved therein does not cause diffusion of the target object. The reason the state of two-dimensional distribution of a target object alters through treatment such as chemical modification is that the object of the present invention cannot be accomplished. Whether or not the state of two-dimensional distribution of a target object has altered can be determined, for example, by comparison with the results of TOF-SIMS analysis of a protein chip for which chemical modification is not performed.

The technique of the above (2) is one in which a substance (sensitizer) that promotes ionization of a target object and increases sensitivity in TOF-SIMS analysis is previously bound to a specific site of a specific target object. This technique is advantageous in that a state of two-dimensional distribution of a specific target object can be detected selectively and at high sensitivity. A drawback with this technique is that the procedure is somewhat intricate, as it is necessary to perform chemical modification treatment in advance for each target object. A method for binding the above sensitizer is not particularly limited, and examples of a method that may be applied include covalent binding and ionic binding, as well as coordinate binding when using a metal complex as a sensitizer. However, since a target object such as a protein that was subjected to chemical modification treatment will be disposed on a substrate, the binding must be stable.

The technique of the above (3) is one in which a substance (sensitizer) that promotes ionization of a target object and increases sensitivity in TOF-SIMS analysis is previously formed on a substrate surface. In this technique, it is important to adequately investigate whether or not the presence of the sensitizer will generate a new problem with respect to nonspecific adsorption. The sensitizer is not particularly limited as long as it is a substance that leads to increased sensitivity in TOF-SIMS analysis, and it may be a substance that does not directly bind with a target object (that is, any substance may be used as long as it has an effect of enhancing ionization efficiency of the target object in a process of generating secondary ions in TOF-SIMS analysis). Although it is preferable that the sensitizer is formed on the uppermost surface of a substrate, it is also possible to provide another substance such as nucleic acid, protein and long-chain carboxylic acid to the extent of a monomolecular film on top of the sensitizer to prevent nonspecific adsorption.

In the present invention, a target object implies a content of cell such as a metabolite and a drug metabolite.

Although chemical modification according to the present invention is not particularly limited as long as, as described above, it produces an effect of enhancing ionization efficiency of a protein in which a content of cell is comprised in a process of generating secondary ions in TOF-SIMS analysis and involves a process that does not alter the two-dimensional distribution state of the protein, the use of a substance containing a metal as a chemical modification agent is preferable. Regarding the kinds of the metal, the studies performed by the present inventors have shown that silver and gold are preferable, and a substance including both thereof is particularly preferable, although metals other than these may also be used as long as they exhibit the above effects.

As one example of a chemical modification technique, a method may be mentioned in which, with respect to a plurality of proteins disposed on a substrate, a silver mirror reaction is utilized to apply silver or silver ion to the proteins. The term "silver mirror reaction" refers to a reaction in which an ammoniacal silver nitrate solution is added to a sample, and then diammine silver(I) ion is reduced to cause silver deposition. Since silver has high affinity for ions, this reaction is particularly effective for a protein comprising Cysteine (Cys). When utilizing this reaction with respect to a protein distributed two dimensionally on a substrate, care is required to ensure the process involved therein does not cause the target object to be diffused. A commercially available reagent (for example, Silver Staining II Kit Wako, manufactured by Wako Pure Chemical Industries, Ltd.) may be used as the reagent in this reaction.

A chemical modification method is not limited to the method described above, and any method may be used as long as it exhibits an effect of enhancing the secondary ion generation efficiency of a target object in TOF-SIMS analysis and involves a process that does not alter the state of two-dimensional distribution of the target object.

Detection (imaging) of a state of two-dimensional distribution of a target object according to the present invention is characterized in that secondary ions is used that can distinguish the target object, and preferably the secondary ions are ions for which the mass-to-charge ratio is 500 or more, and ions having a mass-to-charge ratio of 1000 or more are particularly preferable.

As primary ionic species for use herein, from the viewpoint of ionization efficiency, mass resolution and the like, gallium ions, cesium ions, or in certain cases, gold (Au) ions or the like can be advantageously used. The use of gold ions is preferable in that analysis of an extremely high sensitivity is enabled. At such time, not only Au ions, but also $Au_2$ ions and $Au_3$ ions, which are polyatomic gold ions, can be used, and as there are many cases where it is desired to increase sensitivity in that order, the utilization of polyatomic gold ions is a further preferable form. Bismuth ions and $C_{60}$ ion can be used as other polyatomic ions than gold.

A pulse frequency of a primary ion beam is preferably within the range of 1 kHz to 50 kHz. Preferably, the primary ion beam energy is within the range of 12 keV to 25 keV and the pulse width of a primary ion beam is within the range of 0.5 ns to 10 ns.

In the present invention, to enhance the accuracy of quantitative determination it is necessary to maintain a high mass resolution and to complete measurement in a comparatively short time (one measurement taking in the order of several tens of seconds to several tens of minutes). Therefore measurement is preferably conducted in which the diameter of a primary ion beam is sacrificed to some extent. Specifically, the diameter of a primary ion beam is not focused down to the order of submicrons, and is preferably set within the range of 1 μm to 10 μm.

Further, the present invention can also be applied to a protein chip and a cell array chip on an insulating substrate.

II. Description of the Invention Relating to the Second Aspect of the Present Invention The second aspect of the present invention is characterized in that the target object is caused to emit using a substance for promoting ionization of a target object, to obtain information on the mass of secondary ions that can distinguish the target object that flew. The second aspect is also characterized in that it enables detection (imaging) of a state of two-dimensional distribution of the target object that can be obtained by scanning of a primary ion. A primary beam used for ionizing the target object to cause the target object to emit is not particularly limited as long as it is a beam that can be focused, pulsed and scanned. Examples of substances that can be used for a primary beam include ions, neutral particles, electrons and laser beams. Of these, the use of an ion beam is preferable.

A substance for promoting ionization of a target object according to the present invention is the same as that described in the above I. A method for applying the substance can also be conducted in the same manner as described above. Other conditions and the like may also be the same as described in the above I., unless otherwise specified.

When utilizing the aforementioned chemical modification with respect to a protein, in which a content of cell is comprised, distributed two dimensionally on a substrate without altering the state of two-dimensional distribution, care is required to ensure the procedure does not cause diffusion of the protein. By gently dropping an aqueous solution containing the chemical modification agent onto a site on a substrate on which a protein is disposed, the chemical modification can be performed easily in a one-step process without altering the two-dimensional distribution state of the protein. A method for chemical modification is not limited to the method described above, and any method may be used as long as it has an effect of enhancing the secondary ion generation efficiency of a target object in TOF-SIMS analysis and involves a process that does not alter the state of two-dimensional distribution of the target object.

In the present invention, although a substrate on which a gold substrate or gold film is adhered to the substrate surface is preferable as a substrate on which a protein is disposed as a target of analysis, a substrate is not particularly limited, and as long as it does not comprise a substance emitting secondary ions of a mass that prevents obtainment of the mass information of the protein, an electrically conductive substrate such as a silicon substrate or an insulating substrate such as organic polymer or glass can also be applied for a protein chip. Further, the form of a medium on which a protein is disposed as a target of analysis is not limited to a substrate, and a solid substance of any form, such as a powder or granule, can be used.

The second aspect of the present invention comprises, for example, conducting a step of applying a target object or a substance for promoting ionization, or both thereof, using an ink-jet method.

In a method using an ink-jet method according to the present invention, a substance can be applied without altering the two-dimensional distribution state of a target object by applying droplets of a trace amount of several to several tens of pls per drop to a desired position. When performing treatment over a wide region on a substrate, by applying a large number of droplets of a trace amount, analysis can be performed in which a plurality of target objects are not mixed together on the substrate.

By also forming a target object according to the present invention using an ink-jet method, a plurality of proteins can be disposed at a high density on one substrate, thereby enabling analysis of a greater efficiency. In particular, of the above described analysis methods, TOF-SIMS analysis using ions in a primary beam is advantageous since it provides a high spatial resolution.

When applying a substance promoting ionization with respect to a target object previously distributed two dimensionally on a substrate, after confirming the position beforehand using a light microscope, CCD or the like, analysis of proteins present in a desired region can be performed by applying the substance promoting ionization to the desired region using an ink-jet method. Further, after applying a target object onto a substrate by an ink-jet method, an ionization-promoting agent can be applied onto the top of the target object.

An ionization-promoting substance of the present invention, and/or a target object for analysis of the present invention, can be applied to a target object by an ink-jet method after dissolving the substance in water or a suitable organic solvent and then adding the resulting mixture to an aqueous solution containing a surfactant. Although an organic solvent used herein is not particularly limited, a highly volatile or unstable solvent is not preferable, and from the viewpoint of stability at the time of discharge, preferably a solvent is one for which viscosity was adjusted. In the so-called "ink component" that is other than the ionization-promoting substance and target object for analysis, a component that does not contain a substance that deposits in a solid phase is suitable.

Although an ionization-promoting substance is not particularly limited as long as it is an aqueous substance having an ionization-promoting effect, a substance containing a metal is preferable. In particular, because a silver ion easily forms a complex with an amino acid or peptide, a substance containing silver is favourable. Further, as the above chemical modification agent, a substance containing sodium in place of silver may be used.

The information acquisition apparatus according to the present invention is an apparatus for obtaining information on a target object for measurement using time of flight secondary ion mass spectrometry that has an ion beam irradiation means, an ion beam polarization means, and a detection means for detecting secondary ions from the target object for measurement, which is characterized in that it comprises means for applying droplets. The information acquisition apparatus is further characterized in that the means for applying droplets is means using an ink-jet method.

In the information acquisition apparatus according to the present invention, an ionization-promoting substance and measurement conditions and the like are the same as for the information acquisition method described above.

The information acquisition apparatus according to the present invention comprises a measurement chamber having a time-of-flight secondary ion mass spectroscope, a preliminary evacuation chamber for carrying out normal preliminary evacuation, and a pretreatment chamber having a discharge apparatus for applying droplets.

The pretreatment chamber has a discharge apparatus for applying droplets, a confirmation means for confirming the position of a sample, a sample holder, and a sample stage. The position of the sample stage is controlled, in units of μm, by a position control program. The position control program is the same as the position control program for a sample stage of the measurement chamber. Preferably, for example, measurement can be conducted after the position to which droplets of an ionization-promoting substance were applied by the discharge apparatus is determined inside the measurement chamber and the same position is maintained by an automatic sample stage. The confirmation means is not particularly limited and, for example, may be a light microscope, stereoscopic microscope, or CCD camera.

The pretreatment chamber may also be provided with an evacuation apparatus. In this case, to safeguard the ionization-promoting substance discharge apparatus at the time of evacuation, a valve or the like is preferably provided between the pretreatment chamber and the discharge apparatus.

The discharge apparatus has a print head for use in an ink-jet method, and discharges droplets of several to several tens of pls on any location on the sample. By introducing thereto an ionization-promoting substance solution or protein solution used in the above information acquisition method and conducting discharge, it is possible to dispose a protein on a desired position or apply an ionization-promoting substance to a desired protein. Further, by introducing a staining solution or pigment solution into one part of the ink-jet print head, it is possible to display the X, Y coordinates of a water clear protein solution or perform numbering, thereby providing the advantage of enabling confirmation of a desired position.

III. Description of the Invention Relating to the Third Aspect of the Present Invention An information acquisition method according to the third aspect of the present invention is a method for obtaining information on the distribution state of constituents of tissue from a living organism, in which constituents a metabolic substance in cell is comprised, typified by a protein. According to the present invention, with respect to a section of tissue from a living organism, using a sample comprising a slice that was cleaved such that the cut area thereof is flat, the distribution of an abundance of protein molecules, for example, present on the surface thereof is determined by the TOF-SIMS method.

In tissue from a living organism, peptide chains of a protein molecule as a measurement target are tangled together, and thus cause a decline in the efficiency of generation of secondary ionic species at the time of measurement using the TOF-SIMS method. Therefore, in the third aspect of the present invention, a solution containing a sensitizer can be allowed to act on the surface of a sliced sample of a tissue of a living organism, to thereby enhance the efficiency of generation of secondary ionic species deriving from protein molecules present on the surface. The sensitizer is a substance exhibiting a function that promotes and increases generation of secondary ionic species deriving from protein molecules present on the surface upon irradiation of a primary ion. In order to allow a sensitizer to act directly on protein molecules present on the surface of the sliced sample of a tissue of a living organism, a solution containing the sensitizer is applied to the surface of the slice sample, and maintained in a state where it covers the whole surface. For example, when a weak silver nitrate aqueous solution is used as a solution containing a sensitizer, silver ions dissociated in the aqueous solution act on the peptide chains constituting the protein molecules, thereby generating binding between the silver ions and protein molecules to promote generation of secondary ionic species. In this manner, according to the first aspect of the present invention, the sensitizer itself or a constituent element of the sensitizer acts on peptide chains constituting a protein molecule to generate binding with the peptide chains, culminating in a state where entangled peptide chains of the protein molecule become disentangled. As examples of a sensitizer that can be used in the third aspect of the present invention, in addition to the aforementioned silver nitrate, a salt such as sodium carbonate, a substance (e.g., a metal complex) or a metal colloid containing a metal such as gold or silver and the like may be mentioned. Preferably, a solution containing a sensitizer is in the form of an aqueous solution.

For example, when a primary ion beam is irradiated with respect to the aforementioned protein molecules to which silver ions have bound that are present on the surface of a slice sample, the protein molecules bound with silver ions are partially degraded. This causes generation of secondary ionic species deriving from partially degraded peptide chain fragments that accompany degradation of the protein molecules. Accordingly, the partially degraded peptide chain fragments are more susceptible to ion sputtering than the original protein molecules themselves, and at the same time, the efficiency of generation of fragment ions is also greatly increased. According to the third aspect of the present invention, by utilizing these two actions, when irradiating a primary ion an effect is exhibited that promotes and increases the generation of secondary ionic species deriving from protein molecules present on a surface.

After applying a solution containing a sensitizer onto the surface of a slice sample, maintaining it in a state whereby it covers the whole surface, and allowing it to act on protein molecules present on the surface, the solution containing a sensitizer is removed by washing. Thereafter, since measurement by the TOF-SIMS method is conducted in a high vacuum, moisture contained in the sliced sample of a tissue of a living organism is removed beforehand. Preferably, a vacuum drying method is utilized for this drying treatment. Since a vacuum drying method does not utilize heat for evaporation of moisture, drying can be performed without causing mutual aggregation among protein molecules. At the time of this series of treatments and the subsequent TOF-SIMS analysis, it is preferable that the sliced sample of a tissue of a living organism is handled in a state where it is attached to the surface of a substrate having a flat surface, such as a plate substrate comprising silicon, aluminum, gold or silver or a slide glass or the like. Thereby, the sliced sample of a tissue of a living organism attached to the surface of a substrate having a flat surface can be maintained in a state where it is compactly adhered to the substrate surface after drying also. The surface form of the slice sample obtained after completion of drying treatment reflects the form of the flat substrate surface, exhibiting an even surface.

The information acquisition method according to the third aspect of the present invention is, as mentioned above, an information acquisition method for acquiring information on the mass of a constituent of a target object using a time-of-flight mass spectrometer to obtain information on a distribution of the constituent based on the acquired information, characterized in that the method comprises the steps of:

preparing a sample comprising a constituent of tissue from a living organism as the target object;

conducting a treatment for promoting ionization of an ionic species deriving from the constituent;

irradiating the target object with a focused ion beam to cause the ionic species deriving from the constituent to emit; and measuring an intensity of the flew ionic species using a time-of-flight mass spectrometer to obtain information on a distribution of the constituent based on the measured value.

Herein, constituents of tissue from a living organism include a specific protein. In this case, secondary ionic species deriving from a specific protein are fragment ions originating from partial fragments of peptide chains constituting a specific protein or fragment ions originating from partial fragments of peptide chains having the above sensitizer or components of the sensitizer attached thereto.

For the distribution of ionic intensities of secondary ionic species derived from a specific protein, it is possible to select a form that involves analyzing a two dimensional distribution on the surface of one section of a sample of tissue from a living organism with respect to the ionic intensities of fragment ions derived from the specific protein in question.

Preferably, analysis of the one section of the sample of tissue from a living organism to be analyzed is performed in a state where the section is cooled to a temperature of 0° C. or less.

Further, the solution containing a sensitizer used in a step of treatment with a sensitizer is preferably in the form of an aqueous solution.

Hereunder, a preferred embodiment according to the third aspect of the present invention is described in further detail.

According to the third aspect of the present invention, a sliced sample of a tissue of a living organism provided for analysis is preferably a section of a thickness of approximately several hundred nm to several hundred μm. Various cutting processes can be used as the process for producing a slice from tissue of a living organism as long as a flat cut surface can be obtained. More preferably, to prepare a slice having the aforementioned section thickness, a purpose-built apparatus for producing a section, such as a microtome, is used. Normally, the tissue from a living organism taken as a sample is stored in a cold state to inhibit progress of internal biochemical reactions therein. In the step of cutting the slice sample also, in order to prevent the properties of the protein molecules present thereon from changing, the cutting operation is preferably performed at a temperature of 0° C. or less. Normally the object for cutting of a purpose-built apparatus for producing a section, such as a microtome, is tissue from a living organism in a state where it has been subjected to frozen storage using a freezing medium such as liquid nitrogen.

A sensitizer utilized in the third aspect of the present invention is not particularly limited as long as it is a substance whereby, by allowing it to act on protein molecules beforehand, it exerts an effect of enhancing the efficiency of generation of secondary ions derived from the protein molecules when a primary ion is irradiated in a TOF-SIMS measurement step. For example, a substance containing a metal such as gold or silver or metal ions thereof, that is, a metal complex, a metallic salt compound, or a metal colloid or the like can be advantageously used. A substance containing these metals can bind with a protein molecule. For example, metal ions form ionic bonds with peptide chains constituting a protein molecule, metal complexes coordinate with peptide chains and are immobilized, or a metal colloid particle adheres to a peptide chain. In this state, when a protein molecule is subjected to irradiation with a primary ion, the sensitizer has an effect of enhancing the efficiency of generation of secondary ionic species deriving from the protein molecule such as, for example, fragment ionic species.

Various application means can be utilized as a method of applying a solution containing this sensitizer to the surface of a sliced sample of a tissue of a living organism, as long as the means can apply a desired volume of solution per unit area at good reproducibility. For example, a method in which the solution is applied in the form of droplets onto the surface of a sliced sample of a tissue of a living organism using an ink-jet method or the like may be mentioned. Normally, in tissue from a living organism the site at which protein molecules of interest are present and the abundance thereof are uncertain, and therefore the solution is applied uniformly over the entire surface of the sample comprising a slice of tissue. Thereafter, the sample is allowed to stand still for a predetermined period of time to allow the sensitizer contained in the applied solution layer to act on protein molecules present on the surface. Thereby, the sensitizer is applied to the protein molecules of interest. Depending on the kind of sensitizer used, peptide chains comprising the protein molecules disentangle and may result in easy generation of a large amount of fragment ions at the time of TOF-SIMS analysis. Examples of a solution containing a sensitizer that can be used in an ink-jet method include an aqueous solution having a metal complex or a metallic salt compound uniformly dissolved therein, or a silver nitrate aqueous solution. After completion of treatment to apply a solution containing the sensitizer, any of the solution containing the sensitizer that remains on the surface of the slice sample is removed by washing. Thereafter, it is preferable to subject the entire slice sample to freeze-drying treatment.

Hereafter, the amount of a solution containing a sensitizer to be applied to the surface of a sliced sample of a tissue of a living organism is discussed. Taking as an example the use of silver ions as a sensitizer, with respect to a peptide chain estimated as present on the first layer of the surface of a slice sample, preferably silver ions of a molar ratio selected from the range of an equal amount to 100-fold are applied, and particularly preferably silver ions of a molar ratio of two-fold to ten-fold are applied (i.e. the ratio depends on the length of a peptide chain and the abundance thereof). In general, taking the example of silver ions, the total volume of a sensitizer applied to the surface of a slice sample is approximately $10^{11}$ to $10^{13}$ ions/cm$^2$ (i.e. the level of a monomolecular film or below). The concentration of a sensitizer contained in a sensitizer-containing solution is preferably selected from the range of 1 μmol/mL to 10 μmol/mL.

For example, silver nitrate to be utilized in a sensitizer is dissociated in an aqueous solution to supply monovalent silver ions. When the monovalent silver ions are allowed to act on protein molecules, salt linkage can be formed with respect to carboxy groups present on side chains of amino acid residues comprising the peptide chains thereof. Because a high concentration silver nitrate aqueous solution exhibits an action that causes aggregation of protein molecules, when using a silver nitrate aqueous solution as a sensitizer in the first aspect of the present invention, a weak silver nitrate aqueous solution is used. More specifically, a weak silver nitrate aqueous solution that is of a silver nitrate concentration selected from the range of 1 mmol/L to 10 mmol/L is advantageously used. After allowing a weak silver nitrate aqueous solution to act on a sliced sample of a tissue of a living organism, if the silver nitrate aqueous solution remains on the surface thereof when conducting drying treatment the solution will be condensed to form a high concentration silver nitrate aqueous solution. Therefore it is preferable to remove the solution by washing before the drying treatment.

As mentioned in the foregoing, the efficiency of generation of secondary ionic species in TOF-SIMS is strongly influenced by the form of the surface of the sample used therein. However, by rendering a sliced sample of a tissue of a living organism such that it is attached to the surface of a plate substrate, the surface of the slice sample maintains a flat plane even after drying treatment. Thus, it is possible to substantially eliminate an influence originating from the form of the sample surface that is one factor that impairs the quantitative properties in TOF-SIMS analysis.

Protein constituents present on the surface of a slice sample after drying treatment in a state where the sample is attached to the surface of a flat substrate are analyzed using TOF-SIMS to perform imaging analysis.

Regarding the conditions for the TOF-SIMS analysis, in order to perform two-dimensional imaging, the primary ion beam diameter is preferably selected from the range of 0.1 μm to 10 μm, in accordance with the size of the slice of tissue from a living organism that is the sample to be used as the object of analysis. Regarding the primary ionic species, generally, a metal cation is used, and from the viewpoints of ionization efficiency, mass resolution and the like, gallium ions, cesium ions or, depending on the case, gold (Au) ions or the like can be advantageously used. The use of gold ions is preferable in that analysis of an extremely high sensitivity is enabled. In this case, not only Au ions, but also $Au_2$ ions and $Au_3$ ions, which are polyatomic gold ions, can be used. Since there are numerous cases where it is desired to increase sensitivity in the order of Au ions<$Au_2$ ions<$Au_3$ ions, utilization of polyatomic gold ions is a further preferable form at such time. Other polyatomic ions such as Bi ion or $C_{60}$ or the like with which an equivalent or higher sensitivity can be obtained may be used.

Since surface analysis is being performed, the primary ion beam energy is preferably selected from the range of 12 keV to 25 keV. In order to avoid a build-up (charge-up) of positive charges on the surface of the sample for analysis, pulse irradiation of low energy electrons (approximately several dozen eV) is conducted between the pulses of the primary ion beam to break up the positive charges. The pulse width of a primary ion beam at this time is preferably within the range of 0.5 ns to 10 ns. The pulse frequency is preferably within the range of 1 kHz to 50 kHz. Other conditions, such as an analysis region, a method for scanning a primary ion, and a primary ion dose amount can be appropriately set in accordance with the purpose.

A protein is a polymer composed of peptide chains, and in most cases, it is preferable to measure fragment ions originating from partial fragments of the peptide chains. Preferably, fragment ions to be measured are, at least, ionic species (including those to which a sensitizer or the like is attached) of a mass (m/z) of 500 or more that reflect mass information of partial fragments comprising amino acid residues numbering approximately 5 or more. Ionic species (including those to which a sensitizer or the like is attached) of a mass (m/z) of 1000 or more that reflect mass information of partial fragments comprising amino acid residues numbering approximately 10 or more are particularly preferred. Although secondary ionic species of a mass (m/z) within the range of approximately 0 to 10000 can be simultaneously obtained when employing standard TOF-SIMS analysis conditions, as described above, it is preferable to select as the object of analysis characteristic fragment ions of a mass (m/z) of approximately 500 to 5000 that can distinguish the target protein molecules.

Figure 1B:
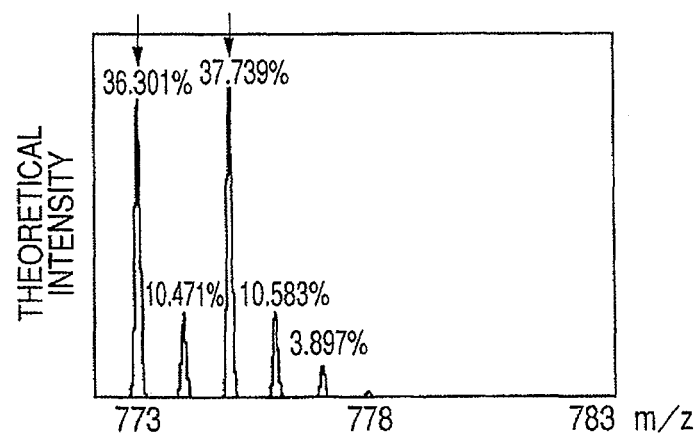

After identifying fragment ions that can distinguish the target protein molecule, an image generated by imaging on an XY plane with peaks (intensity) in the mass spectrum corresponding to the relevant fragment ions from three-dimensional data obtained by TOF-SIMS measurement (for X×Y points on an XY plane, the respective mass spectra exist; this yields four-dimensional data subjected to integrated measurement) is displayed as a two-dimensional distribution image of the aforementioned protein. When a plurality of protein molecules exists as a detection target, this procedure may be repeated. By performing analysis in this manner, as shown in FIGS. 1A and 1B, it is possible to perform analysis for each protein molecule with respect to the distribution of the abundance thereof on a sliced sample of a tissue of a living organism that is the object of analysis. Further, in a separate procedure, by contrasting using microscopic observation an image of the surface of a sample slice corresponding to the measured sample with the image in which peak intensities of secondary ionic species were displayed two dimensionally, it is possible to determine the localized site of the target protein molecules on the section of tissue from a living organism.

Normally, in order to ensure quantitative properties in TOF-SIMS measurement, a primary ion dose amount is $1\times10^{12}$ ion/cm$^2$, which corresponds to an amount for sputtering approximately 1% of a surface. The lower detection limit with respect to a protein on the surface of a sample slice when measuring under this condition, when the mass (m/z) of a fragment ion as the target is 500, is approximately 10 pg/cm$^2$ on the basis of the weight of the fragment ion in question. If the quantitative properties are sacrificed, theoretically an enhanced sensitivity that is higher than the above by two-digits can be expected.

Applying the method of analyzing tissue from a living organism according to the third aspect of the present invention enables direct imaging detection of a protein of interest on a cut section of a cell or tissue from a living organism, thereby making possible a new method for medical diagnosis. At that time, imaging that provides a spatial resolution of approximately 0.1 μm to several μm can be expected.

IV. Description of the Invention Relating to a Fourth Aspect of the Present Invention An information acquisition method according to the fourth aspect of the present invention is a method for obtaining information on the distribution state of constituents of tissue from a living organism, in which constituents a metabolic substance in cell is comprised, typified by a protein. The present invention is characterized in that, with respect to a section of tissue from a living organism, once the surface of the section has been brought into contact with the top of a substrate having a flat surface, for example, a liquid layer containing protein molecules present on the surface of the section is transferred to the substrate surface. Thereafter, the liquid layer containing protein molecules that was transferred to the substrate surface is subjected to drying treatment to adhere the protein components to the surface as dry substances, and analysis can then be conducted using TOF-SIMS. Accordingly, when performing analysis by TOF-SIMS, it is possible to have a flat substrate surface as a substratum, and therefore fluctuations in analysis accuracy arising from the shape of the surface of a measurement target can be substantially eliminated.

Further, as a transfer agent for conducting the transference, it is possible to use an agent having a clean metal surface or metallic oxide surface, or an agent having a flat substrate surface that was subjected to chemical treatment. In tissue from a living organism, there are cases where a protein molecule is present in a state in which the peptide chains thereof are entangled, and upon contacting the protein molecule with the surface of the transfer agent and transferring the protein molecule thereto, the peptide chains disentangle and are transferred as a liquid layer containing the protein components. Examples of a metal surface that can be used as the surface of a transfer agent include silver-metal, gold-metal and the like. Examples of a metal-oxide surface that can be used as the surface of a transfer agent include a titanium oxide ($TiO_2$) surface, a silicon oxide ($SiO_2$) surface, and the like. Examples of a flat substrate surface subjected to chemical treatment include a substrate having a surface to which functional groups such as maleimide groups were introduced by chemical treatment.

The information acquisition method according to the fourth aspect of the present invention is, as mentioned above, an information acquisition method for acquiring information on the mass of a constituent of a target object using a time-of-flight mass spectrometer to obtain information on a distribution of the constituent based on the acquired mass information, characterized in that the method comprises the steps of:

preparing a sample comprising a constituent of tissue from a living organism;

contacting the sample with the surface of a substrate to transfer at least one part of the constituent to the substrate;

irradiating a focused ion beam onto the substrate to which at least one part of the constituent was transferred as the target object to cause an ionic species deriving from the constituent to emit; and measuring an intensity of the flew ionic species using a time-of-flight mass spectrometer to obtain information on a distribution of the constituent based on the measured value.

Herein, constituents of tissue from a living organism include a specific protein. In this case, secondary ionic species deriving from a specific protein are fragment ions originating from partial fragments of peptide chains constituting the specific protein.

As the distribution of ionic intensities of secondary ionic species derived from a specific protein, a form may be selected that analyzes the two dimensional distribution on a surface with respect to the ionic intensities of fragment ions derived from the specific protein. Preferably, a metal surface, metal-oxide surface, or substrate surface utilized in the above transfer step includes a substance that acts on the specified protein to be transferred to enhance the generation efficiency for secondary ionic species deriving from the specified protein.

A flat substrate surface subjected to chemical treatment that is utilized in the transfer step is preferably one subjected to chemical treatment that exhibits an action of enhancing the efficiency of transfer to the surface of the specific protein upon reaction with the specific protein.

A form may also be adopted whereby, preceding the transfer step, after conducting treatment to enhance the transfer efficiency with respect to a specific protein present on one surface of the obtained sample comprising tissue from a living organism, an operation is performed that closely contacts the one surface of the sample comprising tissue from a living organism to a surface for conducting transfer.

For example, a flat substrate surface subjected to chemical treatment that is utilized in the transfer step may be one in which a maleimide group is introduced on the surface thereof as a functional group exhibiting reactivity with respect to the specific protein.

Preferably, analysis is performed in a state where a specific protein that is transferred to the above metal surface, metallic oxide surface, or substrate surface is cooled to a temperature of 0° C. or less.

Hereunder, a preferred embodiment according to the fourth aspect of the present invention is described in further detail.

According to the fourth aspect of the present invention, a silver-metal surface or a titanium oxide surface can be used on the surface of a transfer plate. When these are brought into contact with a protein molecule in the presence of an aqueous solvent, they exhibit an effect of inducing reaction with respect to the peptide chains thereof. An ultrathin oxide layer is commonly present on the surface of silver-metal, and as a result of silver ions or silver oxide supplied from the oxide layer acting on bacteria, functional inhibition or decomposition of biological material comprising a fungus body is caused. Silver(I) oxide functions as an oxidizing agent and may cause an oxidative decomposition reaction.

Titanium oxide, and in particular, a titanium dioxide crystal in a rutile form, is a semiconductor having absorption in an ultraviolet range, and through generation of a photo carrier by irradiation of ultraviolet light, it exhibits various types of catalytic activity. For example, when a titanium dioxide surface is irradiated with ultraviolet light in the presence of an aqueous solvent, it exhibits functions as a photocatalyst to promote oxidative degradation of organic matter adhering to the surface in question.

When a section of tissue from a living organism in a wet condition is brought into contact with a metal surface having this kind of reactivity or a metal-oxide surface that exhibits catalytic activity, a decomposition reaction is induced with respect to a protein molecule present on the section surface. As a result, peptide chains of the protein molecule present on the section surface are partially decomposed and also lose interaction with other biomolecules. In this state, they are transferred to the surface of a transfer plate contacted thereto along with a fluid component contained in the tissue from a living organism.

However, a problem will arise in analysis if a metal surface or metal-oxide surface for conducting transfer is itself contaminated with other protein molecules. Accordingly, prior to the transference process, it is preferable to conduct cleaning of the metal surface or metal-oxide surface for conducting transfer.

A surface composed of silver, gold, silicon or the like can be used as a metal surface for conducting transfer. For cleaning of the surface, a technique which previously exposes a clean metal surface by removing molecules and atoms present on the outermost surface by ion beam sputter etching or the like is effective. An ion gun that is commonly used in TOF-SIMS analysis may be used for the sputter etching treatment. Preferably, a transfer step with respect to a metal surface cleaned by etching treatment is conducted as quickly as possible after the cleaning treatment to avoid re-contamination. Where unavoidable due to operation procedures, a problem does not arise if the surface is exposed to the atmosphere for several minutes to several dozen minutes after providing means for preventing re-contamination of the surface.

A surface composed of silicon oxide, titanium oxide or the like can be used as a metal-oxide surface for conducting transfer. The above ion beam sputter etching technique is also effective for cleaning the metal-oxide surface. In addition, for a metal-oxide surface that has an abundance of resistance to chemicals, a method of cleaning using a wet process can be used. Preferably, the transfer step with respect to the cleaned metal-oxide surface is likewise conducted as quickly as possible after the cleaning treatment to avoid re-contamination.

As an example of a flat substrate surface subjected to chemical treatment utilized for transfer, a surface disclosed in U.S. Pat. No. 6,476,215 in which maleimide groups are introduced onto the surface of a glass substrate may be mentioned. This substrate surface to which maleimide groups were introduced is particularly effective for transferring peptides and proteins having an SH group. More specifically, SH groups present in a peptide or protein to be transferred react with maleimide groups introduced onto the substrate surface to bind the peptide chains to the substrate surface. A silicon substrate having an oxidation zone of a thickness of approximately several tens of nm can also be used as a substrate having a flat surface in place of the glass substrate.

At the time of transfer to the surface of a transfer plate, a protein molecule to be transferred to the surface is preferably transferred at the level of a monomolecular layer. Accordingly, it is preferable that at the time of transfer the pressure of a force for contacting a section of tissue from a living organism in a wet condition to the surface of a transfer plate is regulated within an appropriate range, and in general, a section of the tissue from a living organism may be placed on the surface of a transfer plate (or brought into contact therewith) and left to stand for several seconds. Thus, a liquid layer containing a protein molecule is transferred to the surface of a transfer plate, and preferably the transfer volume is at the monomolecular layer level or below. When using a double wavelength form of ellipsometry, measurement can be performed from a film thickness of about 1 nm. However, it may be considered that a transfer volume in this ellipsometry is too large to allow observation of the liquid layer containing a protein molecule. Accordingly, it is preferable that conditions for the above transfer are suitably adjusted in accordance with the section of tissue from a living organism employed as a target. By keeping the transfer volume of a protein molecule at the monomolecular layer level or below, it is possible for the exposed surface of the substrate to co-exist with the transferred volume, and a sample in that condition can easily generate a large amount of fragment ions in TOF-SIMS analysis (the softest ions are generated when the primary ion does not collide with the protein molecule itself, but rather collides at a site about 0.2 to 0.5 nm away from a site in which the protein is present on the exposed substrate surface; that is, fragment ions that retain a partial structure of the protein are generated).

Further, the distribution state of an abundance of protein molecules transferred to the surface of a transfer plate reflects the distribution state of an abundance of protein molecules on the corresponding section of tissue from a living organism.

According to the fourth aspect of the present invention, the distribution state of the abundance of protein molecules transferred to the surface of a transfer plate is determined using TOF-SIMS. Since determination by TOF-SIMS is conducted in a high vacuum, moisture contained in a liquid layer containing protein molecules that is transferred to the surface of a transfer plate is removed beforehand. Preferably a vacuum drying process is utilized for this drying treatment, however it may also be conducted in the aforementioned preliminary evacuation chamber provided for TOF-SIMS analysis. Since the vacuum drying method does not utilize heat for evaporation of moisture, drying can be performed without causing mutual aggregation among the protein molecules. The distribution state of the abundance of protein molecules transferred to the surface of a transfer plate can maintain the distribution state thereof prior to drying. The sample obtained after completion of drying treatment is in a state where dried protein molecules are attached to and accumulated on the surface of a flat transfer plate. After completion of the transfer process and subsequent drying treatment, while being supplied for TOF-SIMS analysis, a sample that has undergone drying treatment is preferably stored in a clean box or vacuum in order to prevent adhesion of contaminating substances to the surface thereof.

In TOF-SIMS analysis, dried protein molecules present at an irradiated spot are subjected to ion sputtering by irradiation of a primary ion beam, and secondary ionic species derived from the protein molecules are generated. Although, as discussed above, the efficiency of generation of secondary ionic species in TOF-SIMS is strongly influenced by the form of the surface of a sample, by previously transferring the sample onto the aforementioned flat metal surface, metal-oxide surface or the flat substrate surface that underwent chemical treatment the sample surface forms a flat plane, and it is thus possible to substantially eliminate an influence originating from the form of the sample surface, that is one factor that impairs quantitative properties in TOF-SIMS analysis.

Protein constituents transferred onto the surface of a flat transfer plate are analyzed by TOF-SIMS to perform imaging analysis.

Regarding the conditions for the TOF-SIMS analysis, in order to perform two-dimensional imaging the diameter of a primary ion beam is preferably selected from the range of 0.1

μm to 10 μm, in accordance with the size of the slice of tissue from a living organism comprising the sample as the object for analysis. With respect to the primary ionic species, generally, a metal cation is used, and from the viewpoints of ionization efficiency, mass resolution and so forth, gallium ions, cesium ions or, depending on the case, gold (Au) ions or the like can be advantageously used. The use of gold ions is preferable in that analysis of an extremely high sensitivity is enabled. In this case, not only Au ions, but also $Au_2$ ions and $Au_3$ ions, which are polyatomic gold ions, can be used. Since there are numerous cases where it is desirable to increase sensitivity in the order of Au ions<$Au_2$ ions<$Au_3$ ions, utilization of polyatomic gold ions is a further preferable form at such time. Other polyatomic ions such as Bi ion or $C_{60}$ or the like with which an equivalent or higher sensitivity can be obtained may be used.

Since surface analysis is being performed, the primary ion beam energy is preferably selected from the range of 12 keV to 25 keV. In order to avoid a build-up (charge-up) of positive charges on the surface of the sample for analysis, pulse irradiation of low energy electrons (approximately several dozen eV) is conducted between the primary ion beam pulses to break up the positive charges. The pulse width of a primary ion beam at this time is preferably within the range of 0.5 ns to 10 ns. The pulse frequency is preferably within the range of 1 kHz to 50 kHz. Other conditions, such as an analysis region, method for scanning a primary ion, and a primary ion dose amount can be appropriately set in accordance with the purpose.

A protein is a polymer composed of peptide chains, and in most cases it is preferable to measure fragment ions originating from partial fragments of the peptide chains. Preferably, fragment ions to be measured are, at least, ionic species (including those to which a sensitizer or the like is attached) of a mass (m/z) of 500 or more that reflect mass information of partial fragments comprising amino acid residues numbering approximately 5 or more. Ionic species (including those to which a sensitizer or the like is attached) of a mass (m/z) of 1000 or more that reflect mass information of partial fragments comprising amino acid residues numbering approximately 10 or more are particularly preferred. Although secondary ionic species of a mass (m/z) within the range of approximately 0 to 10000 can be simultaneously obtained when employing standard TOF-SIMS analysis conditions, as described above, it is preferable to select as the object of analysis characteristic fragment ions of a mass (m/z) of approximately 500 to 5000 that can distinguish the target protein molecules. When the target object is a metabolite in cell, a mass of the metabolite in cell falls within the range of approximately 50 to 2000, in general.

Figure 2A:
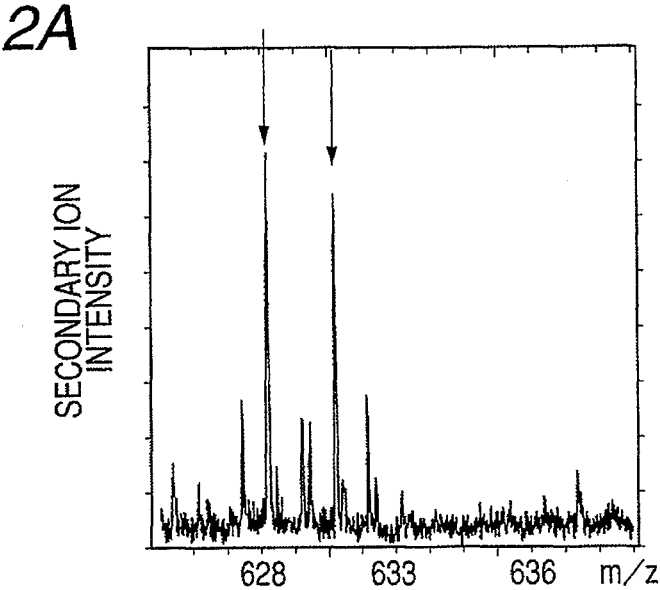
Figure 2B:
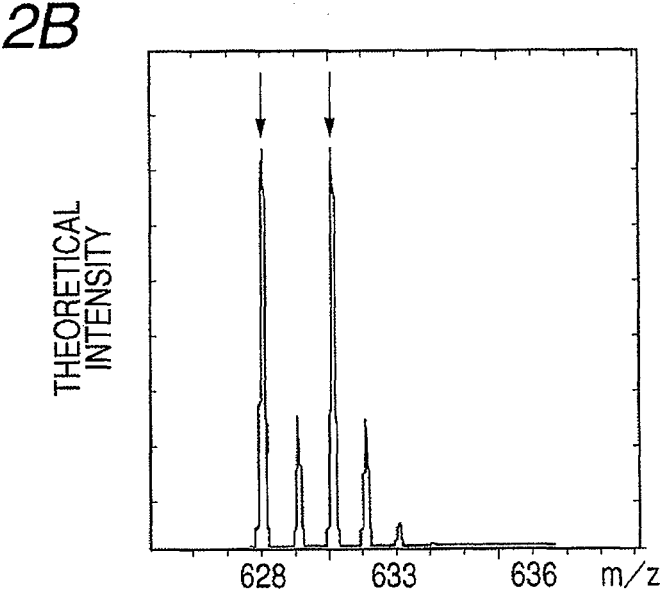
Figure 2C:

After identifying fragment ions that are capable of distinguishing the target protein molecule in which a content of cell is comprised, an image generated by imaging on an XY plane with peaks (intensity) in the mass spectrum corresponding to the relevant fragment ions from three-dimensional data obtained by TOF-SIMS measurement (for X×Y points on an XY plane, the respective mass spectra exist; this yields four-dimensional data subjected to integrated measurement.) is displayed as a two-dimensional distribution image of the aforementioned protein. When a plurality of protein molecules exists as detection targets, the above procedure may be repeated. By conducting analysis in this manner, as shown in FIGS. 2A to 2C, analysis can be performed for each protein molecule with respect to the distribution state of an abundance thereof on a sample surface transferred to the surface of a transfer plate. Further, in a separate procedure, by contrasting in microscopic observation an image of the surface of a sample slice corresponding to the measured sample with the image in which peak intensities of secondary ionic species were displayed two dimensionally, it is possible to determine the localized site of the target protein molecules on the sample surface that transferred to the surface of a transfer plate (corresponding to the cut surface of tissue from a living organism).

Normally, in order to ensure quantitative properties in TOF-SIMS measurement, a dose amount of a primary ion is $1\times10^{12}$ ion/cm$^2$, corresponding to an amount that sputters approximately 1% of a surface. When measuring under this condition, the lower detection limit for a protein on the aforementioned sample surface transferred to the surface of a transfer plate, when the mass (m/z) of a target fragment ion is 500, is approximately 100 fg to 1 pg/cm$^2$ on the basis of the weight of the fragment ion in question. More specifically, sensitivity that is higher by one to two digits in comparison with direct analysis of a section of tissue from a living organism by TOF-SIMS can be expected. If quantitative properties are sacrificed, theoretically a further enhanced sensitivity that is higher than the above by two-digits can be expected.

By using the method for acquiring information according to the fourth aspect of the present invention, it is possible to conduct direct imaging detection for a protein of interest on a cut section of a cell or tissue from a living organism, enabling a new method of medical diagnosis. At this time, imaging that provides a spatial resolution of approximately 0.1 μm to several μm can be expected.

The information acquisition apparatus according to the fourth aspect of the present invention is further characterized in that it comprises: a cleaning apparatus that forms a clean metal surface or metal-oxide surface or an apparatus for conducting chemical treatment on a substrate surface; an apparatus for contacting a sample section of tissue from a living organism with the aforementioned clean metal surface or metal-oxide surface or a substrate surface that was subjected to chemical treatment to transfer protein components present on the section surface; an apparatus for analyzing by TOF-SIMS analysis protein components transferred to the surface of a transfer plate from a section of tissue from a living organism; and a measurement result analysis apparatus for analyzing the state of distribution of a specific protein present on a surface of the sample comprising tissue from a living organism based on the analysis result.

Herein, a transfer apparatus can be designed to have a positioning function whereby it is possible to immobilize a sampled section of tissue from a living organism and transfer protein components present on the section to a specific location on the surface of a transfer plate. Preferably, the apparatus will comprise an apparatus that can regulate a contact force at the time of transfer, in order to transfer protein components to the surface of a transfer plate at the level of a monomolecular layer. From the viewpoint of preventing changes in the properties of protein components, the apparatuses for handling the above sample section of tissue from a living organism and protein components transferred onto the surface of a transfer plate are preferably designed such that all operations are conducted at a temperature of 0° C. or less using a freezing mixture such as liquid nitrogen, excluding steps in which cooling is not possible due to the characteristics of the operations.

In the foregoing, the present invention was described in parts based on the first to fourth aspects. The contents described for the respective aspects can be suitably applied to the other aspects as far as common sense allows, and are not limited to the respective aspect in which description is provided.

Further, the present invention also encompasses a form in which constituent elements of the present invention described in the respective aspects are substituted for constituent elements described in other aspects.

Hereunder, the present invention is explained in further detail referring to examples. The examples described below are illustrative of preferred embodiments of the present invention, and the present invention is not limited to the following specific examples.

EXAMPLE 1

Production of a Chip Spotted with Synthetic Peptide

A Ti film of 5 nm was formed on a silicon substrate that was free of impurities, followed by formation thereon of an Au film of 100 nm. This silicon substrate attached with Au underwent the following treatment prior to spotting thereon of synthetic peptides as described below.

100 µl of hydrogen peroxide solution (30% solution) was inserted into a glass beaker, 300 µl of concentrated sulfuric acid was gently dropped therein, and the resulting mixture was stirred while shaking lightly. Thereafter, the solution was heated to 80° C., and the above silicon substrate attached with Au was washed in this solution for 5 min. The substrate was subsequently taken out, carefully washed with distilled water, and air-dried.

Next, a 10 µM aqueous solution of synthetic peptide I (SEQ ID NO: 1, $C_{21}H_{34}N_{10}O_{11}S$ (average molecular weight: 634.61; mass of molecules comprising elements having the highest isotope ratio: 634.21)) purchased from SIGMA Genosys Japan was prepared. A synthetic peptide containing Cysteine (Cys) was selected since an SH group included in the amino acid residue binds with gold, and it was thus expected that the peptide would be immobilized on the substrate. Further, since silver has a high affinity for sulfur, it was judged that the inclusion of sulfur would be advantageous at the time of modifying the peptide with silver or silver ions in a silver mirror reaction described hereinafter.

The above silicon substrate with Au was spotted with a solution containing the above synthetic peptide I by a pin method. The interval for spotting was 1 mm, and a total of 8×8 spots were formed in the centre part of the substrate. Chips of this type were produced.

EXAMPLE 2

TOF-SIMS of Chip Produced in Example 1

The chip produced in Example 1 was air-dried and analyzed using the TOF-SIMS IV apparatus manufactured by ION-TOF GmbH. The measurement conditions are summarized below.

Primary ion: 25 kV $Ga^+$, 0.6 pA (pulse current value), random scan mode
Pulse frequency of primary ion: 2.5 kHz (400 µs/shot)
Primary ion pulse width: approx. 1 ns
Primary ion beam diameter: approx. 5 µm
Field of measurement: 300 µm×300 µm
Number of pixels of secondary ion image: 128×128
Number of integrations: 256

Upon measuring the positive and negative secondary ion mass spectra under the above conditions, in the positive secondary ion mass spectrum, secondary ions corresponding to the mass of the parent molecule of synthetic peptide I with added Au could be detected. It was possible to obtain an image generated by two-dimensional imaging that reflected the two-dimensional distribution state of the synthetic peptide I using these secondary ions that conformed to the parent ion of synthetic peptide I.

EXAMPLE 3

Silver Mirror Reaction Treatment for Chip Produced in Example 1

The chip produced in Example 1 was air-dried, and in a state where almost all moisture had evaporated, the chip underwent the following treatment (silver mirror reaction).

First, after preparing a silver nitrate solution, ammonia water was added thereto to form an ammonia complex of silver. An ammonia complex of silver was formed to prevent silver changing to silver oxide and separating out when the chemical solution became alkaline, and also to stabilize the oxidation-reduction potential value of silver.

Next, an appropriate amount of an aqueous solution containing the silver ammonia complex was dropped onto the surface of the above substrate and left to stand for 10 min. Thereafter, a weak alkaline aqueous solution in which sodium hydroxide was added to a formaldehyde aqueous solution was dropped onto the surface of the above substrate in an appropriate amount. The substrate was allowed to stand for 10 minutes and then carefully washed with distilled water and air-dried.

EXAMPLE 4

TOF-SIMS Analysis of Chip Treated in Example 3

The positive and negative secondary ion mass spectra were measured under the same conditions as Example 2. As a result, in the positive secondary ion mass spectrum it was possible to detect secondary ions corresponding to the mass of the parent molecule of synthetic peptide I with added Ag and by two oxygen atoms that further attached thereto. An enlarged view of this spectrum region is shown in FIG. 1A, and a theoretical spectrum calculated on the basis of the isotope ratio is shown in FIG. 1B. In FIGS. 1A and 1B, the peaks indicated by arrows correspond to the above ion [(synthetic peptide I)+(Ag)+2(O)]$^+$, and the two arrows respectively correspond to two Ag isotopes (masss: 107, 109). The peak indicated by the arrow on the right side is one comprising $^{109}$Ag, and the m/z value thereof (775.1) roughly matches the theoretical value for [(synthetic peptide I)+($^{109}$Ag)+2 (O)]$^+$. It was possible to obtain an image generated by two-dimensional imaging that reflected the two-dimensional distribution state of the synthetic peptide I using these secondary ions that correspond to the parent ion of synthetic peptide I.

EXAMPLE 5

Preparation of Chip having Synthetic Peptide Spotted on an Insulating Substrate

First, surface treatment of a silica glass substrate was conducted in accordance with a method disclosed in Japanese Patent Application Laid-Open No. H11-187900.

A synthetic quartz substrate with dimensions of 25.4 mm×25.4 mm×1 mm was placed in a rack and immersed overnight in a detergent for ultrasonic cleaning (Branson: GP III) that was diluted to 10% with pure water. Thereafter, ultrasonic cleaning was performed in the detergent for 20 min, and the detergent was then removed by washing with water. After cleaning with pure water, supersonic treatment was further performed for 20 min in a container containing pure water. Next, the substrate was immersed for 10 min in a 1 N sodium hydroxide aqueous solution that was previously heated to 80° C. After water washing followed by cleaning with pure water, the substrate was used in that state without drying as a cleaning agent substrate in the next process.

An aqueous solution containing 1 wt % of a silane coupling agent bound with an amino group, N-β-(aminoethyl)-Y-aminopropyltrimethoxysilane KBM603 (Shin-Etsu Chemical Co., Ltd.), was stirred at room temperature for 2 hrs to hydrolyze intramolecular methoxy groups of the silane compound. After immersing the cleaning agent substrate obtained in the above. (1) in this solution for 1 hr at room temperature, the substrate was washed with pure water and both surfaces of the substrate were then subjected to blowing with nitrogen gas to dry. Next, the substrate was baked for 1 hr in an oven heated to 120° C., thus introducing amino groups onto the substrate surface.

Subsequently, 2.7 mg of N-(Maleimidocaproyloxy) succinimide (Dojindo Laboratories; hereunder referred to as "EMCS") was dissolved in a 1:1 (capacity ratio) dimethyl sulfoxide (DMSO)/ethanol solution to a concentration of 0.3 mg/ml. The above quartz substrate that underwent silane-coupling treatment was immersed in this EMCS solution for 2 hrs at room temperature to react amino groups introduced onto the substrate surface by the silane-coupling treatment with succinimide groups of EMCS. Accompanying this reaction, maleimide groups in EMCS appear on the substrate surface. The substrate was raised out of the EMCS solution, washed with the DMSO/ethanol mixed solvent and then ethanol, and blow-dried with nitrogen gas.

Next, by the same method as Example 1, a solution containing synthetic peptide I was spotted onto the above quartz substrate that underwent surface treatment. More specifically, a 10-μM aqueous solution of synthetic peptide I that was purchased from SIGMA Genosys Japan was prepared, and the above quartz substrate that underwent surface treatment was spotted with this solution by a pin method. The interval between spots was 1 mm, and a total of 8×8 spots were formed in the centre part of the above substrate. A plurality of chips of this type was produced. Since synthetic peptide I comprises an SH group, it was considered that the synthetic peptide I would be immobilized to the substrate surface by addition reaction between this substituent group and a maleimide group.

EXAMPLE 6

Silver Mirror Reaction Treatment of Chip Produced in Example 5

Silver mirror reaction treatment was conducted by the same method as described in Example 3. This sample was provided for the following TOF-SIMS analysis.

EXAMPLE 7

TOF-SIMS Analysis of Chip Produced in Example 5 and Chip Treated in Example 6

Positive and negative secondary ion mass spectra were measured under the same conditions as Example 2. As a result, similar peaks as those exhibited in Example 4 were observed in the positive secondary ion mass spectrum for the chip that underwent silver mirror reaction treatment in Example 6. It was possible to obtain an image generated by two-dimensional imaging that reflected the two-dimensional distribution state of the synthetic peptide I using these secondary ions that correspond to the parent ion of synthetic peptide I.

For the chip (Example 5) that did not undergo silver mirror reaction treatment, two-dimensional ion peaks that conformed to the above parent ion were not observed. In a mass region corresponding to a parent molecule, secondary ion peaks were also not observed.

According to the method of the present invention, for a protein chip in which a plurality of proteins are disposed on a substrate, visualization of the two-dimensional distribution state of each of the plurality of proteins is enabled at a high spatial resolution (up to 1 μm) by conducting imaging measurement using "mass information" of the proteins. The present invention can also be applied to a protein chip on an insulating substrate.

EXAMPLE 8

Spotting of Peptide to Silicon Substrate and Silver Ion Treatment

The substrate used herein was a silicon substrate that was free of impurities which was washed with acetone and deionized water in that order, and then dried. A 10-μM aqueous solution of Morphiceptin (SEQ ID NO: 2, $C_{28}H_{33}N_4O_6$ (average molecular weight: 521.58; mass of molecules comprising elements having the highest isotope ratio: 521.24)) purchased from Phoenix Pharmaceuticals Inc. was prepared using deionized water. The above silicon substrate was spotted with this solution by a micropipetter. After the substrate produced in this manner was desiccated in a refrigerator, the substrate was spotted with approximately 10 μM of silver nitrate solution by a micropipetter so as to overlay the spotted positions with the Morphiceptin solution. After air-drying, the substrate was used for TOF-SIMS analysis.

EXAMPLE 9

TOF-SIMS Analysis of Chip Produced in Example 8

The chip produced in Example 8 was air-dried, and then analyzed using the TOF-SIMS IV apparatus manufactured by ION-TOF GmbH. The measurement conditions are summarized below.

Primary ion: 25 kV $Ga^+$, 1.6 pA (pulse current value), random scan mode
Pulse frequency of primary ion: 7.5 kHz (150 μs/shot)
Primary ion pulse width: approx. 1 ns
Primary ion beam diameter: approx. 3 μm
Field of measurement: 200 μm×200 μm
Number of pixels of secondary ion image: 128×128
Integration time: 600 sec.

Positive and negative secondary ion mass spectra were measured under the above conditions. As a result, in the positive secondary ion mass spectrum, secondary ions corresponding to the mass of the parent molecule of Morphiceptin with added Ag could be detected. An enlarged view of this spectrum region is shown in FIG. 2A, and a theoretical spectrum calculated on the basis of the isotope ratio is shown in FIG. 2B. In FIGS. 2A to 2C, the peaks indicated by arrows correspond to the above ions [(Morphiceptin)+(Ag)]$^+$, and the two arrows respectively correspond to two Ag isotopes (masss: 107, 109). The peak indicated by the arrow on the right side is one comprising $^{109}Ag$, and the m/z value thereof roughly matches the theoretical value (630.15) for [(Morphiceptin)+($^{109}Ag$)]$^+$. It was possible to obtain an image generated by two-dimensional imaging that reflected the two-dimensional distribution state of the Morphiceptin using these secondary ions that conformed with the parent ion of Morphiceptin (FIG. 2C).

EXAMPLE 10

Spotting of Peptide to Glass Substrate (Insulating Substrate) and Silver Ion Treatment The substrate used herein was a synthetic quartz substrate having dimensions of 25.4 mm×25.4 mm×1 mm that was washed with acetone and distilled water in that order, and then dried. A 10 μM aqueous solution of Morphiceptin (SEQ ID NO: 2, $C_{28}H_{33}N_4O_6$ (average molecular weight: 521.58; mass of molecules comprising elements having the highest isotope ratio: 521.24)) purchased from Phoenix Pharmaceuticals Inc. was prepared using deionized water. A small excess of silver nitrate was added thereto. The above synthetic quartz substrate was spotted with this solution by a micropipetter. The substrate produced in this manner was desiccated in a refrigerator, and then used for TOF-SIMS analysis.

EXAMPLE 11

TOF-SIMS Analysis of Chip Produced in Example 10

The chip produced in Example 10 was air-dried, and then analyzed using the TOF-SIMS IV apparatus manufactured by ION-TOF GmbH. The measurement conditions are summarized below.
Primary ion: 25 kV $Ga^+$, 2.4 pA (pulse current value), random scan mode
Pulse frequency of primary ion: 10 kHz (100 μs/shot)
Primary ion pulse width: approx. 1 ns
Primary ion beam diameter: approx. 3 μm
Field of measurement: 200 μm×200 μm
Number of pixels of secondary ion image: 128×128
Integration time: 1200 sec.

Positive and negative secondary ion mass spectra were measured under the above conditions.

Figure 3:
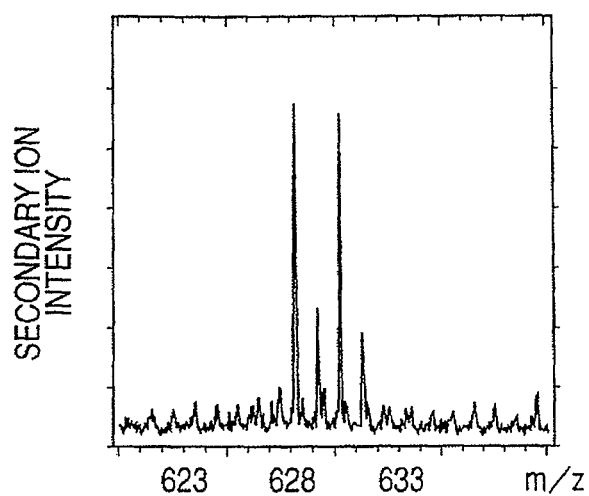
FIG. 3 shows an enlarged view of a section of a measured positive secondary ion mass spectrum according to Example 11.

As a result, in the positive secondary ion mass spectrum, secondary ions could be detected that conformed to the parent ion of Morphiceptin similar to those shown in Examples 8 and 9. An enlarged view of this spectrum region is shown in FIG. 3.

EXAMPLE 12

Spotting of Peptide on Au/Si Substrate and Sodium Ion Treatment

An Au film of 100 nm was formed on a silicon substrate that was free of impurities. This silicon substrate with Au attached thereto was used hereunder. The substrate was produced immediately prior to spotting of a synthetic peptide as described below.

A 10 μM aqueous solution of synthetic peptide II (SEQ ID NO: 3, $C_{84}H_{88}N_{10}O_{20}S$ (average molecular weight: 1589.72; mass of molecules comprising elements having the highest isotope ratio: 1588.59)) purchased from SIGMA Genosys Japan was prepared using deionized water. A small excess of sodium carbonate was added thereto. The above substrate was spotted with the solution by a micropipetter. The thus produced substrate was desiccated in a refrigerator, and then used for TOF-SIMS analysis.

EXAMPLE 13

TOF-SIMS Analysis of Chip Produced in Example 12

The chip produced in Example 12 was air-dried, and then analyzed using the TOF-SIMS IV apparatus manufactured by ION-TOF GmbH. The measurement conditions are summarized below.
Primary ion: 25 kV $Ga^+$, 1.6 pA (pulse current value), random scan mode
Pulse frequency of primary ion: 7.5 kHz (150 μs/shot)
Primary ion pulse width: approx. 1 ns
Primary ion beam diameter: approx. 3 μm
Field of measurement: 200 μm×200 μm
Number of pixels of secondary ion image: 128×128
Number of integrations: 64

Figure 4A:
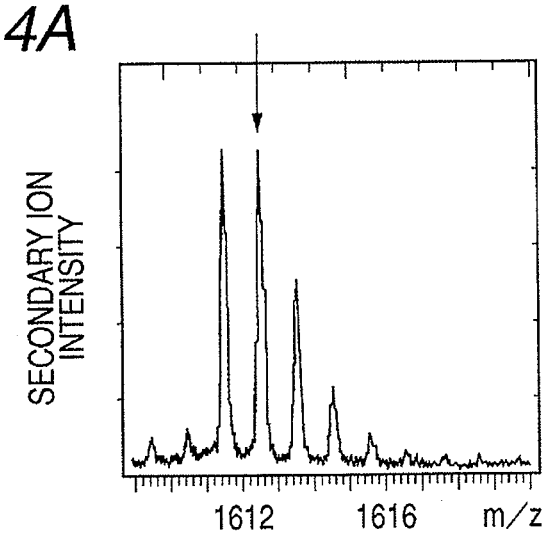
Figure 4B:
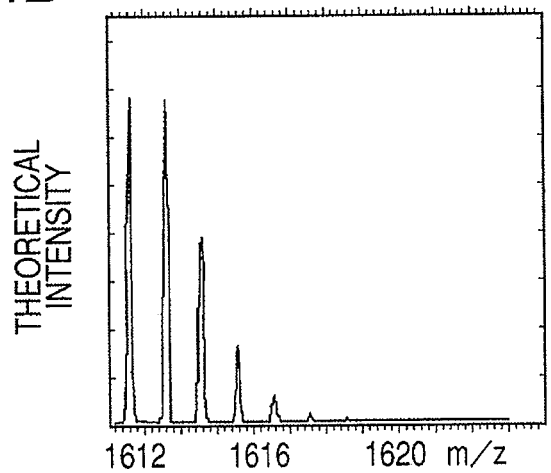
Figure 4C:
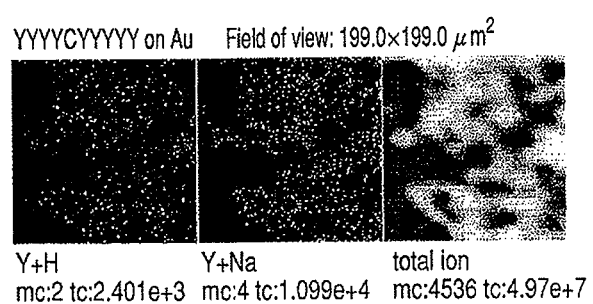

Positive and negative secondary ion mass spectra were measured under the above conditions. As a result, in the positive secondary ion mass spectrum, a secondary ion corresponding to the mass of the parent molecule of synthetic peptide I with added Na could be detected. An enlarged view of this spectrum region is shown in FIG. 4A, and a theoretical spectrum calculated on the basis of the isotope ratio is shown in FIG. 4B. In FIG. 4A, the peak indicated by an arrow corresponds to the above ion [(synthetic peptide II)+(Na)]$^+$, and the m/z value thereof roughly matches the theoretical value (1612.58) for [(synthetic peptide II)+(Na)]. It was possible to obtain an image generated by two-dimensional imaging that reflected the two-dimensional distribution state of the synthetic peptide II using this secondary ion that correspond to the parent ion of synthetic peptide II (FIG. 4C).

COMPARATIVE EXAMPLE 1

Spotting (without Chemical Modification Treatment) of Peptide on Au/Si Substrate and TOF-SIMS Analysis An Au film of 100 nm was formed on a silicon substrate that was free of impurities. This silicon substrate with Au attached thereto was used hereunder. The substrate was produced immediately prior to spotting of a synthetic peptide as described below.

Figure 5:
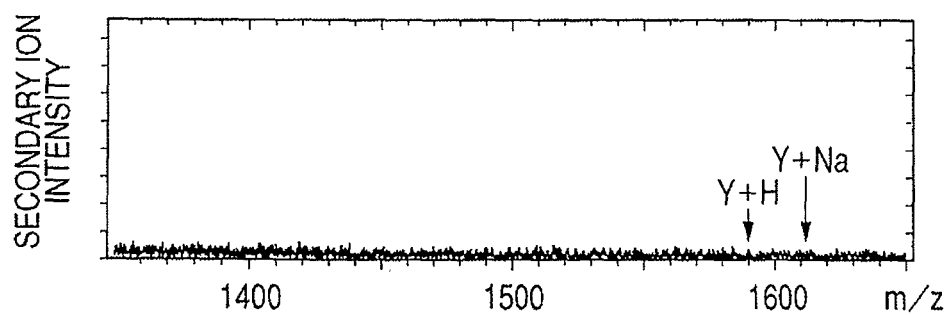
FIG. 5 shows an enlarged view of a section of a measured positive secondary ion mass spectrum according to comparative Example 1.

A 10-μM aqueous solution of synthetic peptide II (SEQ ID NO: 3, $C_{84}H_{88}N_{10}O_{20}S$ (average molecular weight: 1589.72; mass of molecules comprising elements having the highest isotope ratio: 1588.59)) purchased from SIGMA Genosys Japan was prepared using deionized water. The above substrate was spotted with the solution by a micropipetter. The thus produced substrate was desiccated in a refrigerator, and then used for TOF-SIMS analysis. Positive and negative secondary ion mass spectra were measured under the same conditions as Example 13. As a result, in the positive secondary ion mass spectrum, a peak conforming to the parent ion of synthetic peptide II that was similar to that observed in Example 13 was not observed (FIG. 5).

EXAMPLE 14

Spotting of Peptide on Silicon Substrate and Silver Ion Treatment

The substrate used herein was a silicon substrate that was free of impurities which was washed with acetone, isopropanol and deionized water in that order, and then dried.

Thereafter, the following three kinds of peptide were dissolved in deionized water:

Peptide 1: Morphiceptin (manufactured by Phoenix Pharmaceuticals Inc.; SEQ ID NO: 2; average molecular weight: 521.58)

Peptide 2: Ghrelin(1-5)-NH2(Des-Octanoyl 3) (manufactured by Phoenix Pharmaceuticals Inc.; SEQ ID NO: 4; average molecular weight: 508.10)

Peptide 3: synthetic peptide I (manufactured by SIGMA Genosys Japan; SEQ ID NO: 1; average molecular weight: 634.61)

As an ionization-promoting substance, silver nitrate was similarly dissolved in deionized water.

Next, aqueous solution containing 1 wt % of acetylene alcohol (product name: acetylenol EH, manufactured by Kawaken Fine Chemicals Co., Ltd.) was prepared and added to each of the above peptide-containing solutions and the silver nitrate solution. Each solution was adjusted to bring to a final concentration of 40 µmol/l.

These solutions were filled into ink tanks for use with a Bubble Jet® printer (product name: BJF850; manufactured by Canon Inc.), and the tanks were installed in a Bubble Jet® print head. The Bubble Jet® printer used herein had been modified to enable printing to a flat plate. The discharge rate at the time of spotting was 4 pl/droplet, and the scope of spotting was 150 dpi in an area of 10 mm×10 mm in the centre of a substrate, that is, discharge at a pitch of 169 µm.

Figure 6:
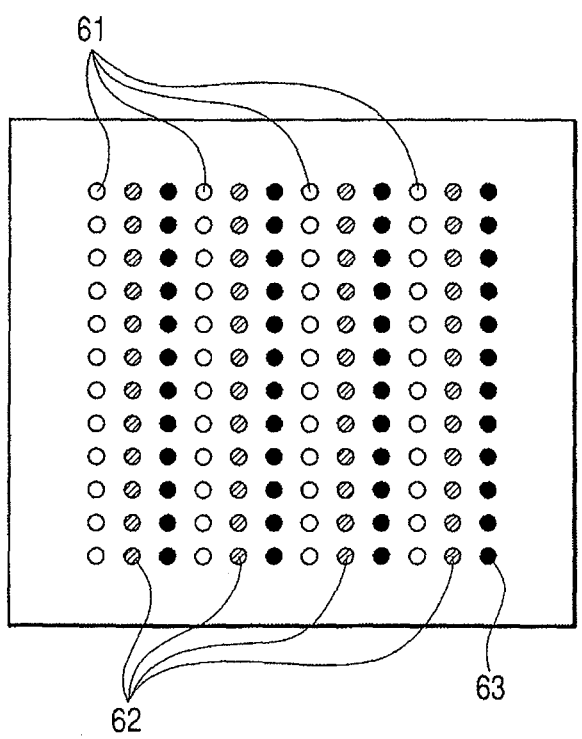
FIG. 6 is a view showing the schematic layout of peptides according to Example 14.

Subsequently, the above silicon substrate was mounted on a tray for use with a flat plate of the printer, and fluid containing the peptides was spotted onto the silicon substrate. The number of discharged droplets was 12 droplets×12 rows=144 droplets. The droplets were discharged in the order of peptide 1 (numeral 61), peptide 2 (numeral 62), peptide 3 (numeral 63), peptide 1, peptide 2 . . . so as to dispose the different kinds of peptides in order on the substrate. Each row of peptides was disposed such that they were arrayed in the same manner (FIG. 6).

After drying the thus-produced substrate at room temperature, the substrate was spotted with the above silver nitrate solution in the same positions as the above peptide spots in a condition overlaying the peptide spots. The substrate was air-dried and then used for TOF-SIMS analysis.

EXAMPLE 15

TOF-SIMS Analysis of Chip Produced in Example 14

The chip produced in Example 14 was air-dried, and then analyzed using the TOF-SIMS IV apparatus manufactured by ION-TOF GmbH. The measurement conditions are summarized below.

Primary ion: 25 kV $Ga^+$, 2.4 pA (pulse current value), random scan mode
Pulse frequency of primary ion: 10 kHz
Primary ion pulse width: approx. 1 ns
Primary ion beam diameter: approx. 3 µm
Field of measurement: 300 µm×300 µm
Number of pixels of secondary ion image: 128×128
Integration time: 210 sec.

Figure 7A:
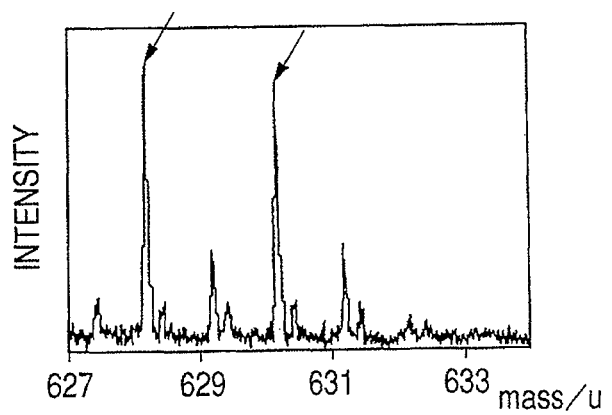
Figure 7B:
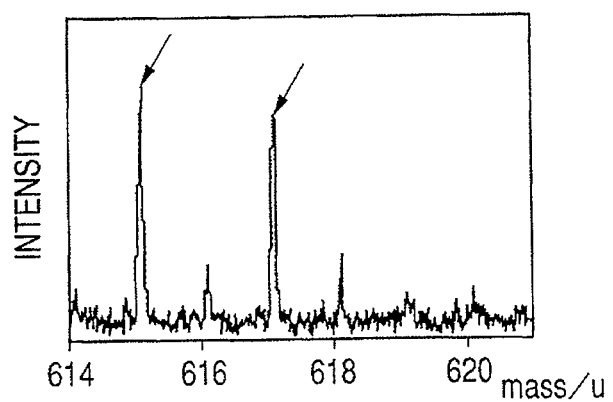
Figure 7C:
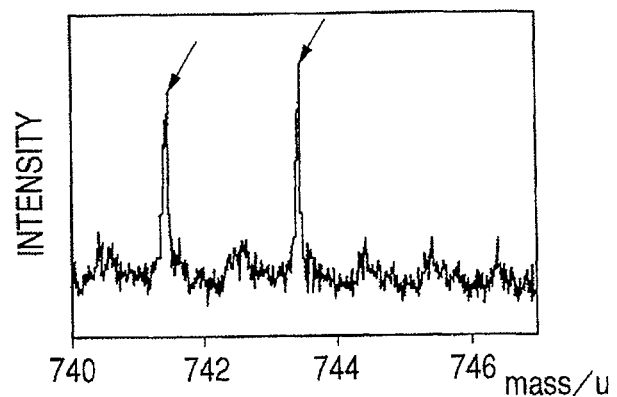

Positive and negative secondary ion mass spectra were measured under the above conditions. As a result, in the positive secondary ion mass spectrum, secondary ions corresponding to the mass of the parent molecule of each peptide with added Ag could be detected. FIGS. 7A to 7C shows enlarged views of this spectrum region for each peptide. In FIGS. 7A to 7C, the peaks indicated by arrows correspond to the above ions [(each peptide molecule)+(Ag)]$^+$, and the two arrows respectively correspond to two Ag isotopes (masss: 107, 109).

Figure 8:
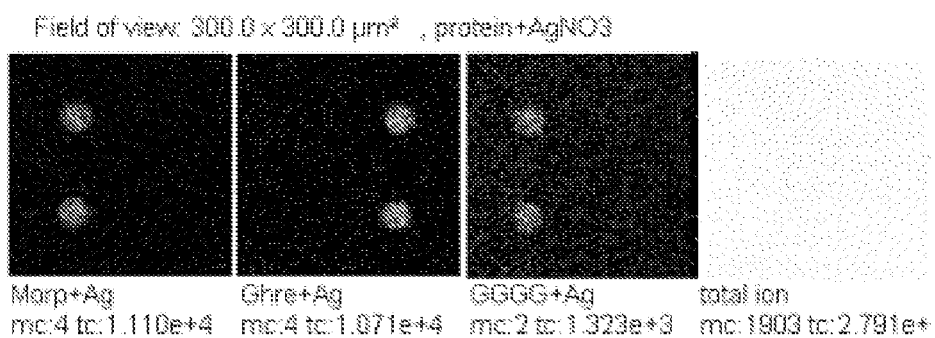
FIG. 8 shows secondary ion images generated using the spectra shown in FIGS. 7A to 7C.

Two-dimensional images were generated using the secondary ions corresponding to the mass of the parent molecule of each peptide with added Ag, whereby the images shown in FIG. 8 were obtained that were in accordance with the m/z values of the selected secondary ions. By comparing these images with the printing file of the printer, it was confirmed that the images obtained corresponded to the mass of each peptide+Ag in the order of spotting by the printer.

It was thus found that when analyzing a plurality of kinds of proteins, analysis can be performed at one time without the plurality of kinds of proteins mixing together by putting the plurality of kinds of proteins together on one substrate by spotting using a Bubble Jet® printer.

EXAMPLE 16

Spotting of Peptide and Silver Ion Mixed Solution onto a Silicon Substrate

A silicon substrate treated in the same manner as in Example 14 was prepared. Three kinds of peptide solution and silver nitrate solution were also prepared in the same manner as in Example 14.

Peptide 1 solution and silver nitrate solution, peptide 2 solution and silver nitrate solution, and peptide 3 solution and silver nitrate solution were respectively mixed immediately prior to being filled into ink tanks of the same Bubble Jet® printer as used in Example 14. Spotting was then performed in the same manner as Example 14 to prepare a substrate for analysis.

The thus produced substrate for analysis was analyzed in the same manner as in Example 15, and similar images were obtained.

EXAMPLE 17

Spotting of Peptide and Sodium Ion Mixed Solution onto a Silicon Substrate

A substrate for analysis was prepared that was produced in the same manner as in Example 16, with the exception that the ionization-promoting agent was changed from a silver nitrate solution to a sodium carbonate solution. This was analyzed in the same manner as in Example 15.

Two-dimensional images were generated using the secondary ions corresponding to the mass of the parent molecule of each peptide with added Na, whereby images in accordance with the m/z values of the selected secondary ions were obtained. By comparing these images with the printing file of the printer, it was confirmed that the images obtained corresponded to the mass of each peptide+Na in the order of spotting by the printer.

EXAMPLE 18

Spotting of Peptide to Glass Substrate and Silver Ion Treatment

After cleaning a one-inch square synthetic quartz substrate with a detergent and washing with deionized water, the substrate was washed with acetone, isopropyl alcohol and butyl acetate in that order, and dried for 20 min at 120° C.

The thus prepared substrate was spotted with the same three kinds of peptide solutions and silver nitrate as used in Example 14. The solutions were arrayed in the same manner as Example 14 to produce a substrate with the respective spots.

EXAMPLE 19

TOF-SIMS Analysis of Chip Produced in Example 18

The chip produced in Example 18 was air-dried, and then analyzed using the TOF-SIMS IV apparatus manufactured by ION-TOF GmbH. The measurement conditions are summarized below.
Primary ion: 25 kV Ga$^+$, 0.6 pA (pulse current value), random scan mode
Pulse frequency of primary ion: 2.5 kHz (400 µs/shot)
Primary ion pulse width: approx. 1 ns
Primary ion beam diameter: approx. 3 µm
Field of measurement: 300 µm×300 µm
Number of pixels of secondary ion image: 128×128
Integration time: 1200 sec.

Positive and negative secondary ion mass spectra were measured under the above conditions. As a result, in the positive secondary ion mass spectrum, secondary ions conforming to the parent ion of each peptide that were the same as those exhibited in Example 15 could be detected. Two-dimensional images were generated using these ions, whereby images were obtained that were in accordance with the disposition position of each peptide.

That is, the effect for an electrically conductive substrate was similarly obtained for an insulating substrate.

EXAMPLE 20

Information Acquisition Apparatus with Pretreatment Chamber

Figure 9:
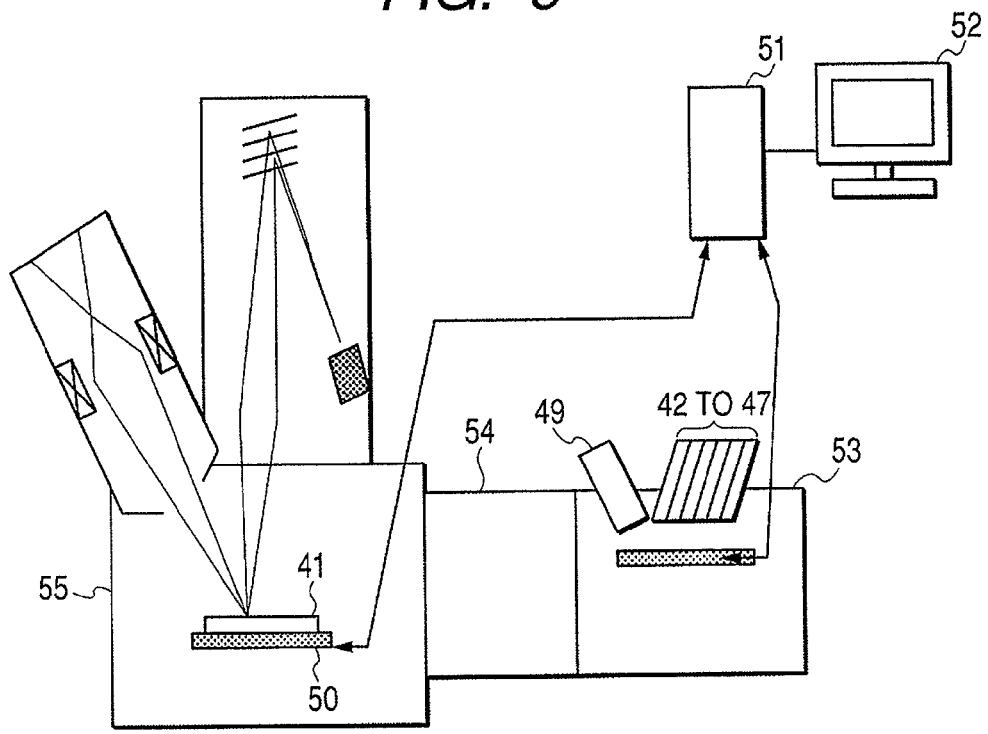
FIG. 9 is a schematic diagram of an information acquisition apparatus according to Example 20.

FIG. 9 is a schematic diagram of an information acquisition apparatus according to this example.

Hereunder, an example is described of analyzing a sample 41 on which a plurality of peptides is mixed, using an apparatus according to the present invention. The apparatus according to the present invention is an analysis apparatus having a time-of-flight mass spectrometer that uses an Au ion gun as a primary beam and applies droplets by means of a discharge apparatus that is contained in a pretreatment chamber. A sample 41 for measurement was one having a plurality of peptides in a mixed state on a synthetic quartz substrate.

Peptides to be placed on the sample were prepared, organic solvent of the same kind as that used in Example 14 was added thereto, and the solutions were filled into nozzles 42 to 45. In this example, the following four kinds of peptide were filled into respectively different nozzles.
Peptides 1 to 3: same as for Example 14
Peptide 4: Casoxin D (manufactured by Phoenix Pharmaceuticals Inc.; SEQ ID NO: 5; average molecular weight: 866.03)

Further, a silver nitrate solution was filled into a separate nozzle 46, and magenta ink used as ink for a normal Bubble Jet printer was filled into another nozzle 47.

Thereafter, a silicon substrate 48 was placed in the apparatus, and spotted with each peptide and the magenta ink at a pitch of 200 dpi., followed by being spotted with Silver nitrate solution was further spotted on only the above peptide spots.

Next, while confirming the respective positions with a CCD 49, silver nitrate solution at desired positions on the sample 41 for measurement in the same manner. The spotted positions were recorded as positional information of a sample stage 50 by a control computer 51.

After drying the thus-produced sample 41 and silicon substrate 48 in a pretreatment chamber 53, preliminary evacuation was performed in an introduction chamber 54, and the sample 41 was transferred to a measurement chamber 55. Thereafter, the silicon substrate 48 was subjected to positive and negative secondary ion mass spectrum analysis under the following conditions.
Primary ion: 25 kV Au$^{3+}$, 0.05 pA (pulse current value), random scan mode
Pulse frequency of primary ion: 5 kHz (200 µs/s)
Primary ion pulse width: approx. 1 ns
Field of measurement: 300 µm×300 µm
Number of pixels of secondary ion image: 128×128
Number of integrations: 128

As a result, in the positive secondary ion mass spectrum, secondary ions corresponding to the mass of the parent molecule of each peptide with added Ag could be detected.

Figure 10:
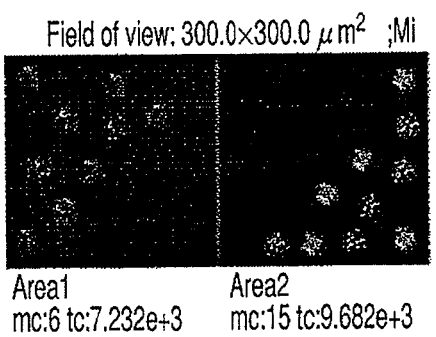
FIG. 10 shows secondary ion images according to Example 20.
Figure 11A:
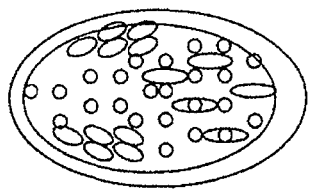
FIGS. 11A, 11B, 11C and 11D are views that schematically show the information acquisition method according to the third aspect of the present invention.
Figure 11B:
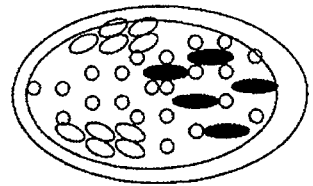
Figure 11C:
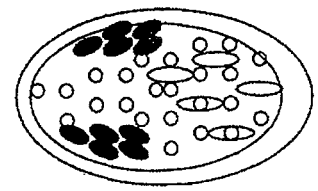
Figure 11D:
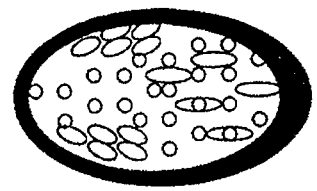
Figure 12A:
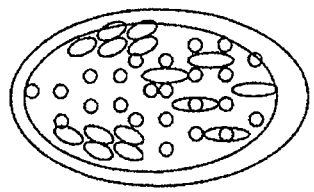
FIGS. 12A, 12B, 12C, 12D and 12E are views that schematically show the information acquisition method according to the fourth aspect of the present invention.
Figure 12B:
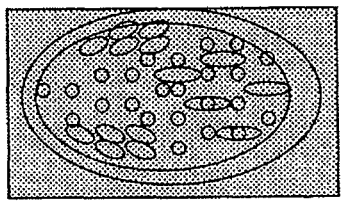
Figure 12C:
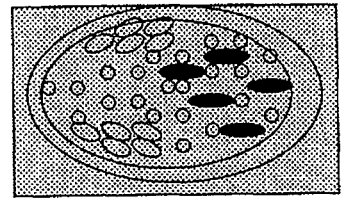
Figure 12D:
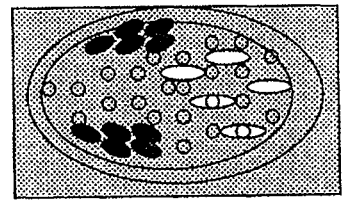
Figure 12E:
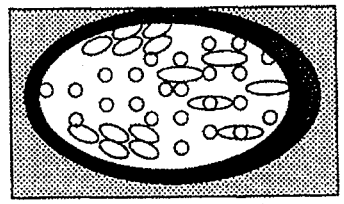

Using each of these ions, imaging analysis of the sample 41 for measurement was performed. The stage was moved to the previously recorded position to conduct analysis of the sample 41. As a result, in areas in which silver nitrate was spotted, as shown in "Area 2" images in right and "Area 1" image in left of FIG. 10, secondary ions corresponding to the mass of peptide 1 with added Ag (the "Area 2" image) and secondary ions corresponding to the mass of peptide 3 with added Ag (the "Area 1" image) were detected. It was thus determined from images generated by secondary ion imaging that the sample 41 for measurement was a sample having peptide 1 and peptide 3 present thereon in a two-dimensional distribution state.

EXAMPLE 21

In this example, a case is described in which a sliced sample of a tissue of a living organism is attached to a flat surface of a slide glass, and the surface of the slice sample is treated with a sensitizer according to the procedure described below.

As an example of a protein molecule to be used as a measurement target, 4N1K peptide associated with cancer tissue that is disclosed in Japanese Patent Application Laid-Open No. 2004-77268 or the like may be mentioned. As a sample comprising tissue from a living organism that is an object of analysis, a lesion section that is cancer tissue is excised. When using 4N1K as a target, digestive treatment is performed on the surface of a slice sample prepared from this lesion section using protease (matrix metalloprotease 3: MMP3). Subsequently, the slice sample is attached to a substrate having a flat surface, such as a glass substrate, and immobilized thereon.

Thereafter, silver nitrate solution is applied onto the surface of the slice sample using the Bubble Jet® method or the like. As the silver nitrate solution used as a solution containing a sensitizer, for example, an aqueous solution containing AgNO$_3$ at a concentration of 0.5 mmol/L can be used. The solution is applied to the surface of the slice sample at, for example, a coating weight of 0.5 µl/cm$^2$. In a state where the surface is covered by this AgNO$_3$ solution, the sample is left to stand at room temperature for 10 min, to allow solute ion species that are dissolved in the solution to act on protein components present on the surface of the slice sample. Thereafter, AgNO$_3$ solution that is covering the surface is removed by washing with pure water.

Next, in a condition where the sample is attached to the flat surface of a substrate, the slice sample that was treated with a sensitizer is dried in a vacuum dryer for 5 min, and then dried in a preliminary evacuation chamber of a TOF-SIMS analysis apparatus.

In TOF-SIMS analysis, as a fragment ion originating from 4N1K peptide that is a fragment peptide of TSP-1 protein (a protein that participates in cancer progression and vascularisation in cancer tissue), a cationic species (including one to which a sensitizer is attached) comprising a partial structure of SEQ ID NO: 6 can be used. Herein, a step of protease digestion treatment with respect to the surface of a slice sample may also be performed after attaching the slice sample to a substrate surface to immobilize it thereto.

In this kind of tissue from a living organism, there are cases where the properties of a target protein molecule may change due to physiological activity of enzyme proteins coexisting in the tissue. Therefore, it is preferable that the temperature of a sample is maintained at 0° C. or less for the series of operations.

When performing imaging measurement by TOF-SIMS of protein components present on the surface of a sliced sample of a tissue of a living organism, one example of TOF-SIMS analysis conditions that can be used according to this example are shown below. Herein, the range of the field of measurement can be appropriately altered in consideration of the size of the slice sample itself, or the putative distribution state (localized site or the like) for a specific protein molecule.

<Primary Ion>
Primary ion: 25 keV Ga$^+$, 0.1 pA (pulse current value), random scan mode
Pulse frequency of primary ion: 10 kHz (100 μs/shot)
Primary ion pulse width: 1 ns (Duty ratio 1/100,000)
Primary ion beam diameter: approx. 0.5 μm
Electron bombardment: pulse current flow 10 μA; pulse width 96 μs
<Secondary Ion>
Secondary ion detection mode: positive
Voltage for extracting secondary ions: 2 kV
Field of measurement: 50 μm×50 μm
Number of pixels of secondary ion image: 128×128
Number of integrations: 256
Holder temperature: 0° C.

Under the above measurement conditions, the spatial resolution in two-dimensional imaging corresponds to 1 μm.

Further, under the above primary ion irradiation conditions, a sputtering depth corresponds to within the scope of a depth of approximately 1 nm from the outermost surface of a dried slice sample.

In contrast, for a dried slice sample that was only subjected to vacuum drying and was not treated with the above sensitizer, in general, it is difficult to detect at high sensitivity fragment ions of a mass (m/z) of 500 or greater that can distinguish a target protein molecule.

By utilizing the method illustrated herein it is possible to grasp the distribution state of constituents of tissue from a living organism, and based on the distribution state it is possible to distinguish, for example, whether tissue employed as a measurement target is a malignant cancer or a benign tumor. Thus, the diagnosis of disease is enabled.

EXAMPLE 22

In this example, the capability of two-dimensional analysis by TOF-SIMS was confirmed employing bovine serum albumin (BSA) immobilized on a gold surface as a target.

In accordance with the method disclosed in Japanese Patent Application Laid-Open No. 2004-085546, an aqueous solution containing bovine serum albumin (BSA) was discharged by the Bubble Jet® method to form spots comprising BSA on a previously cleaned gold substrate.

The BSA used herein was a commercially available product (manufactured by Sigma Aldrich Japan), and the concentration of protein in the solution was approximately 1 μM. The discharge volume per spot was approximately 4 pl and the diameter of the spots was 50 μm. The applied BSA formed spots on the monomolecular layer level on the cleaned gold substrate surface. BSA contains a cysteine residue, and thus it is intended to bind peptide chains to the surface by reaction between SH group of the cysteine side chain and gold atoms on the surface.

After formation of spots, the substrate is allowed to air-dry for 10 min. Herein, the surface concentration of BSA in the above spots corresponds to 0.05 μmol/cm$^2$. Thereafter, TOF-SIMS analysis was conducted using the TOF-SIMS IV apparatus manufactured by ION-TOF GmbH. The measurement conditions are summarized below.

<Primary Ion>
Primary ion: 25 keV Ga$^+$, 0.1 pA (pulse current value), random scan mode
Pulse frequency of primary ion: 10 kHz (100 μs/shot)
Primary ion pulse width: 1 ns (Duty ratio 1/100,000)
Primary ion beam diameter: approx. 0.5 μm
Electron bombardment: pulse current flow 10 μA; pulse width 96 μs
<Secondary Ion>
Secondary ion detection mode: positive
Voltage for extracting secondary ions: 2 kV
Field of measurement: 50 μm×50 μm
Number of pixels of secondary ion image: 128×128
Number of integrations: 256
Holder temperature: 0° C.

Under the above conditions, TOF-SIMS analysis was conducted on a spot section of a diameter of approximately 50 μm. As a result thereof, peaks corresponding to the following fragment ions and the like were observed:

$C_4H_6N^+$ (m/z=68) and $C_4H_8N^+$ (m/z=50) that are considered to be fragment ions derived from Pro residue;
$CH_3N^+$ (m/z=29), $C_2H_7N_3^+$ (m/z=73), $C_4H_{10}N_3^+$ (m/z=100), $C_4H_{11}N_3^+$ (m/z=101), and $C_5H_8N_3^+$ (m/z=110) that are considered to be fragment ions derived from Arg residue;
$C_9H_8N^+$ (m/z=130), $C_{10}H_{11}N^+$ (m/z=145) and $C_{11}H_8NO^+$ (m/z=170) that are considered to be fragment ions derived from Trp residue; and
$C_2H_6NS^+$ (m/z=76) and $CHS^+$ (m/z=45) that are considered to be fragment ions derived from Cys residue.

Further, an outline corresponding to the spots of a diameter of approximately 50 μm that were formed by the Bubble Jet® method could be confirmed from a two-dimensional distribution image generated using these secondary ions.

Thus, when TOF-SIMS analysis was performed for BSA of a monomolecular layer level that was present on a clean gold surface, fragment ions characteristic to amino acid residues that can be utilized for distinguishing BSA were detected as secondary ions. Further, by plotting the ionic intensities of these secondary ions two-dimensionally, a two-dimensional distribution image of a spatial resolution up to about 1 μm could be obtained.

In addition, based on the measured ionic intensities of the secondary ions, it is estimated that the lower limit for the surface density of a protein molecule that allows two-dimensional imaging analysis according to the above measurement conditions corresponds to approximately 1 pmol/cm$^2$.

Herein, the diameter of a primary ion beam may also be focused to the level of 0.1 μm, whereby a two-dimensional distribution image of a higher resolution can be obtained by employing measurement conditions that utilize a primary ion of a smaller beam diameter and an increased number of pixels. In order to generate characteristic secondary ions that correspond to partial fragments of a peptide chain that can be utilized to distinguish BSA, where necessary, a sensitizer may be provided with respect to the peptide chain prior to TOF-SIMS analysis.

EXAMPLE 23

In this example, a case is described in which, according to the procedure described below, a sliced sample of a tissue of a living organism is brought into contact with a flat metal surface and two-dimensional distribution analysis is performed utilizing the TOF-SIMS method for each kind of the protein molecules transferred onto the metal surface from the surface of the slice sample.

Hereunder, steps of transferring protein molecules present on the surface of a section of excised tissue from a living organism to a gold substrate surface, and analyzing the two-dimensional distribution of each kind of protein using TOF-SIMS are summarized.

As an example of a protein molecule to be used as a measurement target, 4N1K peptide associated with cancer tissue that is disclosed in Japanese Patent Application Laid-Open No. 2004-77268 or the like may be mentioned. As a sample comprising tissue from a living organism as the object for analysis, a lesion section that is cancer tissue is excised. When using 4N1K as a target, digestive treatment is performed on the surface of a slice sample prepared from this lesion section using protease (matrix metalloprotease 3: MMP3). Next, the section surface of the slice sample that was digested with protease is contacted with the top of a substrate having a flat gold surface. Thereafter, the sample is allowed to dry in a preliminary evacuation chamber of a TOF-SIMS analysis apparatus, and provided for TOF-SIMS analysis.

To avoid influencing the two-dimensional distribution of protein components transferred onto the surface of a substrate it is also possible to conduct the above protease digestion treatment after completing the step of transferring the protein components to the substrate surface. More specifically, when the peptide chains of protein components transferred onto the substrate surface are bound to the surface, even though protease digestion treatment is carried out thereafter the two-dimensional distribution state itself is maintained.

In order to generate secondary ions that are characteristic to the amino acid sequences of the peptide chains that can be utilized for distinguishing 4N1K peptide, where necessary, a sensitizer may be provided with respect to the peptide chains prior to TOF-SIMS analysis.

In this kind of tissue from a living organism, there are cases where the properties of a target protein molecule may change due to physiological activity of enzyme proteins coexisting in the tissue. Therefore, it is preferable that the temperature of a sample is maintained at 0° C. or less for the series of operations.

The TOF-SIMS analysis conditions employed in this example can be the same as the conditions described in the above Example 22, and the range of the field of measurement can be appropriately adjusted after considering the size of the slice sample to undergo transferring, or the putative distribution state (localized site or the like) of a protein molecule that is a target of analysis.

In this example, as a secondary ionic species derived from 4N1K peptide, a cationic species (including one to which a sensitizer is attached) comprising a partial structure of SEQ ID NO: 6 can be used.

By utilizing the method illustrated above it is possible to grasp the distribution state of constituents of tissue from a living organism, and based on the distribution state it is possible to distinguish, for example, whether tissue employed as a measurement target is a malignant cancer or a benign tumor. Thus, the diagnosis of disease is enabled.

EXAMPLE 24

In this example, a developed disease diagnosis method from that shown in Example 21 is described.

The method of this example is different from the method of Example 21 in performing the digestive treatment with protease after the attachment of a lesion section to a substrate and in carrying out the digestive treatment by applying droplets containing the digestive enzyme through an ink-jet method such as Bubble-jet method that the method of this example is different from the method in Example 21. In the application by ink-jet method, a surfactant may be added to the liquid to be ejected so as to obtain a stable ejection. The performing of both the specific decomposition of the target protein by the digestive enzyme and the application of a substance for promoting ionization of the ionic species deriving from a resultant of the decomposition by means of an ink-jet method in TOF-SIMS analysis makes it possible to obtain a two-dimensional distribution reflecting the initial distribution of the protein in the lesion tissue. For the purpose of specifying the protein still not decomposed through the ion species of the resultant of the decomposition, various known database of resultants of proteome analysis can be utilized.

EXAMPLE 25

Spotting of Cells to Glass Substrate (Insulation Substrate) and Silver Ion Treatment The substrate used herein was a synthetic quartz substrate having dimensions of 25.4 mm×25.4 mm×1 mm that was washed with acetone and distilled water in that order, and then dried. A 10-µM aqueous solution of Morphiceptin (SEQ ID NO: 2, $C_{28}H_{33}N_4O_6$ (average molecular weight: 521.58; mass of molecules comprising elements having the highest isotope ratio: 521.24)) purchased from Phoenix Pharmaceuticals Inc. was prepared using deionized water. The above silicon substrate was spotted with this solution by a micropipetter.

Normal human epidermal melanocyte (manufactured by Kurabo Industries Ltd.) was cultured in a manner recommended by Kurabo Industries Ltd., and the cultured products are collected and suspended in a physiological salt solution in which silver nitrate had been previously solved to have a concentration of 10 µM so that a suspension of 4000 cell/ml was obtained. Then, the quartz substrated was spotted with 5 µl of the suspension by a micropipetter. After a drying, the resulting substrate was appropriately washed with a deionized water, and dried again.

EXAMPLE 26

TOF-SIMS Analysis of Cell Prepared in Example 25

The cell-adhered glass substrate prepared in Example 25 was analyzed using the TOF-SIMS IV apparatus manufactured by ION-TOF GmbH. The measurement conditions are summarized below.

Primary ion: 25 kV Ga$^+$, 2.4 pA (pulse current value), random scan mode

Pulse frequency of primary ion: 10 kHz (100 μs/shot)
Primary ion pulse width: approx. 1 ns
Primary ion beam diameter: approx. 3
Field of measurement: 200 μm×200
Number of pixels of secondary ion image: 128×128
Integration time: 1200 sec.

Positive and negative secondary ion mass spectra were measured under the above conditions. In the positive secondary ion mass spectrum, a two-dimensional distribution state of the following amino acids was observed: Phe, Pro, Tyr, Gly, Leu, Ala, Ile, Met, Glu, Thr, Arg, Asn, Ser, Gln, His, Lys, Val and Asp. As a result, it can be seen that the content of cell, in particular, amino acids as a metabolic substance in cell were observed as a two-dimensional imaging.

EXAMPLE 27

Adhering of a Section of Liver Tissue to Glass Substrate (Insulation Substrate) and Silver Ion Treatment The substrate used herein was a synthetic quartz substrate having dimensions of 25.4 mm×25.4 mm×1 mm that was washed with acetone and distilled water in that order, and then dried.

Caffeine were orally administrated to four rats bred to laboratory animals in an amount of 0.5 mg caffeine per kg of weight of rat. Livers of the rats were extracted after 51, 30, 60 and 120 minutes, respectively. The livers were then sectioned in a conventional manner and adhered on the glass. After drying, the resulting sections were washed with a physiological salt solution containing silver nitrate and then with a deionized water in the same manner as in Example 25, and dried again.

EXAMPLE 28

TOF-SIMS Analysis of Sections of Tissue Prepared in Example 27

The glass substrate with the sections of tissue prepared in Example 27 was analyzed using the TOF-SIMS IV apparatus manufactured by ION-TOF GmbH. The measurement conditions are summarized below.
Primary ion: 25 kV Ga$^+$, 2.4 pA (pulse current value), random scan mode
Pulse frequency of primary ion: 10 kHz (100 μs/shot)
Primary ion pulse width: approx. 1 ns
Primary ion beam diameter: approx. 3 μm
Field of measurement: 200 μm×200 μm
Number of pixels of secondary ion image: 128×128
Integration time: 1200 sec.

Positive and negative secondary ion mass spectra were measured under the above conditions. In the positive secondary ion mass spectrum, Spectrums of the following compounds were two-dimensionally observed in a celllike form: (1) caffeine, (2) any of theobromine, theophylline and paraxanthine as a result of eliminating one methyl group from caffeine, (3) methylxanthine as a result of eliminating two methyl groups from caffeine, and (4) xanthine as a result of eliminating three methyl groups from caffeine. Strong signal intensities of spectrum were observed at the metabolite end with time from the administration. As a result, it can be seen that the content of cell, in particular, drug metabolites in a living organism were observed as a two-dimensional imaging.

Sequence Listing Free Text
<210> 1
<223> synthesized peptide as a sample for TOF-SIMS analysis
<210> 2
<223> synthesized peptide as a sample for TOF-SIMS analysis
<210> 3
<223> synthesized peptide as a sample for TOF-SIMS analysis
<210> 4
<223> synthesized peptide as a sample for TOF-SIMS analysis
<210> 5
<223> synthesized peptide as a sample for TOF-SIMS analysis
<210> 6
<223> a partial structure of 4N1K peptide This application claims priorities from Japanese Patent Application Nos. (1) 2003-270350 filed on Jul. 2, 2003, (2)2003-321418 filed on Sep. 12, 2003, (3)2003-340787 filed on Sep. 30, 2003, (4)2004-154617 filed on May 25, 2004 and (5)2004-380052 filed on Dec. 28, 2004, which are hereby incorporated by reference herein.

---

SEQUENCE LISTING

```
<160> NUMBER OF SEQ ID NOS: 6

<210> SEQ ID NO 1
<211> LENGTH: 10
<212> TYPE: PRT
<213> ORGANISM: Artificial
<220> FEATURE:
<223> OTHER INFORMATION: synthesized peptide as a sample for TOF-SIMS
      analysis

<400> SEQUENCE: 1

Gly Gly Gly Gly Cys Gly Gly Gly Gly Gly
1               5                   10

<210> SEQ ID NO 2
<211> LENGTH: 4
<212> TYPE: PRT
<213> ORGANISM: Artificial
<220> FEATURE:
```

```
<223> OTHER INFORMATION: synthesized peptide as a sample for TOF-SIMS
      analysis

<400> SEQUENCE: 2

Tyr Pro Phe Pro
1

<210> SEQ ID NO 3
<211> LENGTH: 10
<212> TYPE: PRT
<213> ORGANISM: Artificial
<220> FEATURE:
<223> OTHER INFORMATION: synthesized peptide as a sample for TOF-SIMS
      analysis

<400> SEQUENCE: 3

Tyr Tyr Tyr Tyr Cys Tyr Tyr Tyr Tyr Tyr
1               5                   10

<210> SEQ ID NO 4
<211> LENGTH: 5
<212> TYPE: PRT
<213> ORGANISM: Artificial
<220> FEATURE:
<223> OTHER INFORMATION: synthesized peptide as a sample for TOF-SIMS
      analysis

<400> SEQUENCE: 4

Gly Ser Ser Phe Leu
1               5

<210> SEQ ID NO 5
<211> LENGTH: 7
<212> TYPE: PRT
<213> ORGANISM: Artificial
<220> FEATURE:
<223> OTHER INFORMATION: synthesized peptide as a sample for TOF-SIMS
      analysis

<400> SEQUENCE: 5

Tyr Val Pro Phe Pro Pro Phe
1               5

<210> SEQ ID NO 6
<211> LENGTH: 10
<212> TYPE: PRT
<213> ORGANISM: Artificial
<220> FEATURE:
<223> OTHER INFORMATION: a partial structure of 4N1K peptide

<400> SEQUENCE: 6

Lys Arg Phe Tyr Val Val Met Trp Lys Lys
1               5                   10
```

What is claimed is:

1. A method for acquiring information on an object in a tissue of a living organism, comprising the steps of:
applying a solution containing a digestive enzyme to decompose the object in the tissue specifically to a surface of the tissue so as to obtain the decomposed object;
irradiating the surface of the tissue with an ion beam to ionize the decomposed object after applying the solution containing the digestive enzyme to decompose the object in the tissue specifically; and
acquiring information on the mass of the decomposed object that ionizes using time-of-flight secondary ion mass spectrometry after irradiating the surface of the tissue with an ion beam.

2. The method according to claim 1, wherein the object is selected from the group consisting of a protein, a peptide and a metabolite.

3. The method according to claim 1, wherein the tissue is a section of tissue from a living organism.

4. The method according to claim 1, wherein the target object is a protein molecule within the tissue, and the method further comprising conducting two-dimensional imaging with respect to a distribution state of an abundance of the protein molecule.

* * * * *